US010405548B2

(12) United States Patent
Walter et al.

(10) Patent No.: US 10,405,548 B2
(45) Date of Patent: *Sep. 10, 2019

(54) FUNGICIDAL COMPOSITIONS

(71) Applicant: Syngenta Crop Protection, LLC, Greensboro, NC (US)

(72) Inventors: Harald Walter, Basel (CH); Urs Neuenschwander, Rheingelder (CH); Ronald Zeun, Stein (CH); Josef Ehrenfreund, Basel (CH); Hans Tobler, Basel (CH); Camilla Corsi, Basel (CH); Clemens Lamberth, Basel (CH)

(73) Assignee: Syngenta Crop Protection LLC, Greensboro, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/953,825

(22) Filed: Apr. 16, 2018

(65) Prior Publication Data

US 2018/0228157 A1 Aug. 16, 2018

Related U.S. Application Data

(62) Division of application No. 15/363,501, filed on Nov. 29, 2016, now Pat. No. 9,949,482, which is a division of application No. 14/017,632, filed on Sep. 4, 2013, now Pat. No. 9,538,755, which is a division of application No. 11/573,277, filed as application No. PCT/EP2005/008748 on Aug. 11, 2005, now Pat. No. 8,536,089.

(30) Foreign Application Priority Data

Aug. 12, 2004 (GB) .................................. 0418047.7

(51) Int. Cl.
| | |
|---|---|
| A01N 43/56 | (2006.01) |
| A01N 43/78 | (2006.01) |
| A01N 25/00 | (2006.01) |
| A01N 43/36 | (2006.01) |
| A01N 43/653 | (2006.01) |
| A01N 43/707 | (2006.01) |

(52) U.S. Cl.
CPC ............. *A01N 43/56* (2013.01); *A01N 25/00* (2013.01); *A01N 43/36* (2013.01); *A01N 43/653* (2013.01); *A01N 43/707* (2013.01); *A01N 43/78* (2013.01)

(58) Field of Classification Search
CPC .... A01N 43/56; A01N 43/707; A01N 43/653; A01N 43/36; A01N 43/78; A01N 25/00
See application file for complete search history.

(56) References Cited

U.S. PATENT DOCUMENTS 7,807,714 B2 * 10/2010 Brandi .................. A01N 37/46
514/229.2
2003/0036480 A1 2/2003 Schelberger et al.

FOREIGN PATENT DOCUMENTS

| | | |
|---|---|---|
| DE | 19939841 A1 | 5/2000 |
| EP | 0209234 A2 | 1/1987 |
| EP | 0256503 A2 | 2/1988 |
| WO | 9710716 A1 | 3/1997 |
| WO | 9916314 A1 | 4/1999 |
| WO | 2003/074491 A1 | 9/2003 |
| WO | 2005/063710 A1 | 7/2005 |

OTHER PUBLICATIONS

Anonymous, Research Disclosure 346121, Mixtures of Fungicides, 1998, Research Disclosure, 2 pages.
Anonymous, Research Disclosure 429052, Azoxystrobin Compositions, 2000, Research Disclosure, 8 pages.
International Search Report and Written Opinion for International Patent Application No. PCT/EP2005/008748, dated Nov. 23, 2005.

* cited by examiner

*Primary Examiner* — John Pak
*Assistant Examiner* — Andriae M Holt
(74) *Attorney, Agent, or Firm* — Baker & Hostetler LLP; Toni-Junell Herbert

(57) ABSTRACT

The invention relates to fungicidal compositions comprising as active ingredient a combination of components A) and B) as defined in the patent claims, to a method of controlling phytopathogenic diseases on crop plants using such a composition and to a method of protecting natural substances of vegetable and/or animal origin and/or their processed forms using such a composition.

4 Claims, No Drawings

FUNGICIDAL COMPOSITIONS

This application is a divisional of U.S. patent application Ser. No. 15/363,501 filed 29 Nov. 2016 which is a divisional of U.S. patent application Ser. No. 14/017,632 filed Sep. 4, 2013, now issued U.S. Pat. No. 9,538,755 issued Jan. 10, 2017, which is a divisional of U.S. patent application Ser. No. 11/573,277 filed Feb. 6 2007, now issued U.S. Pat. No. 8,536,089 issued Sep. 17, 2013, which is a 371 of International Application No. PCT/EP2005/008748 filed Aug. 11, 2005, which claims priority to GB 0418047.7 filed Aug. 12, 2004, all the contents of which are incorporated herein by reference.

The present invention relates to novel fungicidal compositions for the treatment of phytopathogenic diseases of useful plants, especially phytopathogenic fungi, to a method of controlling phytopathogenic diseases on useful plants and to a method of protecting natural substances of vegetable and/or animal origin and/or their processed forms.

It is known that certain o-cyclopropyl-carboxanilide derivatives have biological activity against phytopathogenic fungi, e.g. known from WO 03/074491 where their properties and methods of preparation are described. On the other hand various fungicidal compounds of different chemical classes are widely known as plant fungicides for application in various crops of cultivated plants. However, crop tolerance and activity against phytopathogenic plant fungi do not always satisfy the needs of agricultural practice in many incidents and aspects.

There is therefore proposed in accordance with the present invention a method of controlling phytopathogenic diseases on useful plants or on propagation material thereof, which comprises applying to the useful plants, the locus thereof or propagation material thereof a combination of components A) and B) in a synergistically effective amount, wherein component A) is a compound of formula I

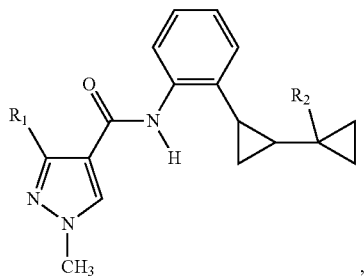

(I)

wherein

R$_1$ is trifluoromethyl or difluoromethyl and

R$_2$ is hydrogen or methyl; or a tautomer of such a compound; and component B) is a compound selected from the group consisting of Benomyl (62); Carbendazim (116); Fuberidazole (419); Thiabendazole (790); Thiophanate (1435); Thiophanate-methyl (802); Chlozolinate (149); Iprodione (470); Procymidone (660); Vinclozolin (849); Azaconazole (40); Bitertanol (84); Bromuconazole (96); Cyproconazole (207); Difenoconazole (247); Diniconazole (267); Diniconazole-M (267); Epoxiconazole (298); Fenarimol (327); Fenbuconazole (329); Fluquinconazole (385); Flusilazole (393); Flutriafol (397); Hexaconazole (435); Imazalil (449); Imibenconazole (457); Ipconazole (468); Metconazole (525); Myclobutanil (564); Nuarimol (587); Oxpoconazole (607); Pefurazoate (618); Penconazole (619); Prochloraz (659); Propiconazole (675); Prothioconazole (685); Pyrifenox (703); Simeconazole (731); Tebuconazole (761); Tetraconazole (778); Triadimefon (814); Triadimenol (815); Triflumizole (834); Triforine (838); Triticonazole (842); Benalaxyl (56); Furalaxyl (410); Metalaxyl (516); Mefenoxam (Metalaxyl-M) (517); Ofurace (592); Oxadixyl (601); Aldimorph; Dodemorph (288); Fenpropimorph (344); Fenpropidin (343); Spiroxamine (740); Tridemorph (830); Edifenphos (290); Iprobenfos (IBP) (469); Isoprothiolane (474); Pyrazophos (693); Benodanil (896); Carboxin (120); Fenfuram (333); Flutolanil (396); Furametpyr (411); Mepronil (510); Oxycarboxin (608); Thifluzamide (796); Bupirimate (98); Dimethirimol (1082); Ethirimol (1133); Cyprodinil (208); Mepanipyrim (508); Pyrimethanil (705); Diethofencarb (245); Azoxystrobin (47); Famoxadone (322); Fenamidone (325); Kresoxim-methyl (485); Metominostrobin (551); Picoxystrobin (647); Pyraclostrobin (690); Trifloxystrobin (832); Fenpiclonil (341); Fludioxonil (368); Quinoxyfen (715); Biphenyl (81); Chloroneb (139); Dichloran (240); Etridiazole (321); Quintozene (PCNB) (716); Tecnazene (TCNB) (767); Tolclofos-methyl (808); Dimethomorph (263); Carpropamid (122); Diclocymet (237); Fenoxanil (338); Fthalide (643); Pyroquilon (710); Tricyclazole (828); Fenhexamid (334); Polyoxin (654); Pencycuron (620); Cyazofamid (185); Zoxamide (857); Blasticidin-S (85); Kasugamycin (483); Streptomycin (744); Validamycin (846); Cymoxanil (200); Iodocarb (3-Iodo-2-propynyl butyl carbamate); Propamocarb (668); Prothiocarb (1361); Dinocap (270); Fluazinam (363); Fentin acetate (347); Fentin chloride; Fentin hydroxide (347); Oxolinic acid (606); Hymexazole; Octhilinone (590); Fosetyl-Aluminium (407); Phosphoric acid; Tecloftalam; Triazoxide (821); Flusulfamide (394); Ferimzone (351); Diclomezine (239); Anilazine (878); Arsenates; Captafol (113); Captan (114); Chlorothalonil (142); Copper (diverse salts); Copper Ammoniumcarbonate; Copper octanoate (170); Copper oleate; Copper sulphate (87; 172; 173); Copper hydroxide (169); Dichlofluanid (230); Dithianon (279); Dodine (289); Ferbam (350); Folpet (400); Guazatine (422); Iminoctadine (459); Mancozeb (496); Maneb (497); Mercury; Metiram (546); Propineb (676); Sulphur (754); Thiram (804); Tolylfluanid (810); Zineb (855); Ziram (856); Acibenzolar-S-methyl (6); Probenazole (658); Benthiavalicarb; Benthiavalicarb-isopropyl (68); Iprovalicarb (471); Diflumetorim (253); Ethaboxam (304); Flusulfamide (394); Methasulfocarb (528); Silthiofam (729); *Bacillus pumilus* GB34; *Bacillus pumilus* strain QST 2808; *Bacillus subtilis* (50); *Bacilus subtilis*+PCNB+Metalaxyl (50; 716; 516); Cadmium chloride; Carbon disulfide (945); Bordeaux mixture (87); Cedar leaf oil; Chlorine; Cinnamaldehyde; Cycloheximide (1022); Fenaminosulf (1144); Fenamiphos (326); Dichloropropene (233); Dichlone (1052); Formaldehyde (404); *Gliocladium virens* GL-21 (417); Glyodin (1205); Hexachlorobenzene (434); Iprovalicarb (471); Manganous dimethyldithiocarbamate; Mercuric chloride (511); Nabam (566); Neem oil (hydrophobic extract); Oxytetracycline (611); Chinomethionat (126); Paraformaldehyde; Pentachloronitrobenzene (716); Pentachlorophenol (623); paraffin oil (628); Polyoxin D zinc salt (654); Sodium bicarbonate; Potassium bicarbonate; Sodium diacetate; Sodium propionate; TCMTB; Benalaxyl-M; Boscalid (88); Fluoxastrobin (382); Hexaconazole (435); Metrafenone; Oxine Copper (605); Penthiopyrad; Perfurazoate; Tolyfluanid; *Trichoderma harzianum* (825); Triphenyltin hydroxide (347); *Xanthomonas campestris* (852); Paclobutrazol (612); 1,1-bis(4-chlorophenyl)-2-ethoxyethanol (IUPAC-Name) (910); 2,4-dichlorophenyl benzenesulfonate (IUPAC-/Chemical Abstracts-Name) (1059); 2-fluoro-N-methyl-N-1-naphthylacetamide (IUPAC-Name) (1295); 4-chlorophenyl phenyl sulfone (IUPAC-Name) (981); abamectin (1); acequinocyl (3); acetoprole [CCN]; acrinathrin (9); aldicarb (16); aldoxycarb (863); alpha-cypermethrin (202); amidithion (870); amidoflumet [CCN]; amidothioate (872); amiton (875); amiton hydrogen oxalate (875); amitraz (24); aramite (881); arsenous oxide (882); AVI 382 (compound code); AZ 60541 (compound code); azinphos-ethyl (44); azinphos-methyl (45); azobenzene (IUPAC-Name) (888); azocyclotin (46); azothoate (889); benomyl (62); benoxafos (alternative name) [CCN]; benzoximate (71); benzyl benzoate (IUPAC-Name) [CCN]; bifenazate (74); bifenthrin (76); binapacryl (907); brofenvalerate (alternative name); bromocyclen (918); bromophos (920); bromophos-ethyl (921); bromopropylate (94); buprofezin (99); butocarboxim (103); butoxycarboxim (104); butylpyridaben (alternative name); calcium polysulfide (IUPAC-Name) (111); camphechlor (941); carbanolate (943); carbaryl (115); carbofuran (118); carbophenothion (947); CGA 50'439 (development code) (125); chino-methionat (126); chlorbenside (959); chlordimeform (964); chlordimeform hydrochloride (964); chlorfenapyr (130); chlorfenethol (968); chlorfenson (970); chlorfensulphide (971); chlorfenvinphos (131); chlorobenzilate (975); chloromebuform (977); chloromethiuron (978); chloropropylate (983); chlorpyrifos (145); chlorpyrifos-methyl (146); chlorthiophos (994); cinerin I (696); cinerin II (696); cinerins (696); clofentezine (158); closantel (alternative name) [CCN]; coumaphos (174); crotamiton (alternative name) [CCN]; crotoxyphos (1010); cufraneb (1013); cyanthoate (1020); cyhalothrin (196); cyhexatin (199); cypermethrin (201); DCPM (1032); DDT (219); demephion (1037); demephion-O (1037); demephion-S (1037); demeton (1038); demeton-methyl (224); demeton-O (1038); demeton-O-methyl (224); demeton-S (1038); demeton-S-methyl (224); demeton-S-methylsulphon (1039); diafenthiuron (226); dialifos (1042); diazinon (227); dichlofluanid (230); dichlorvos (236); dicliphos (alternative name); dicofol (242); dicrotophos (243); dienochlor (1071); dimefox (1081); dimethoate (262); dinactin (alternative name) (653); dinex (1089); dinex-diclexine (1089); dinobuton (269); dinocap (270); dinocap-4 [CCN]; dinocap-6 [CCN]; dinocton (1090); dinopenton (1092); dinosulfon (1097); dinoterbon (1098); dioxathion (1102); diphenyl sulfone (IUPAC-Name) (1103); disulfiram (alternative name) [CCN]; disulfoton (278); DNOC (282); dofenapyn (1113); doramectin (alternative name) [CCN]; endosulfan (294); endothion (1121); EPN (297); eprinomectin (alternative name) [CCN]; ethion (309); ethoate-methyl (1134); etoxazole (320); etrimfos (1142); fenazaflor (1147); fenazaquin (328); fenbutatin oxide (330); fenothiocarb (337); fenpropathrin (342); fenpyrad (alternative name); fenpyroximate (345); fenson (1157); fentrifanil (1161); fenvalerate (349); fipronil (354); fluacrypyrim (360); fluazuron (1166); flubenzimine (1167); flucycloxuron (366); flucythrinate (367); fluenetil (1169); flufenoxuron (370); flumethrin (372); fluorbenside (1174); fluvalinate (1184); FMC 1137 (development code) (1185); formetanate (405); formetanate hydrochloride (405); formothion (1192); formparanate (1193); gamma-HCH (430); glyodin (1205); halfenprox (424); heptenophos (432); hexadecyl cyclopropanecarboxylate (IUPAC-/Chemical Abstracts-Name) (1216); hexythiazox (441); iodomethane (IUPAC-Name) (542); isocarbophos (alternative name) (473); isopropyl O-(methoxyaminothiophosphoryl)salicylate (IUPAC-Name) (473); ivermectin (alternative name) [CCN]; jasmolin I (696); jasmolin II (696); jodfenphos (1248); lindane (430); lufenuron (490); malathion (492); malonoben (1254); mecarbam (502); mephosfolan (1261); mesulfen (alternative name) [CCN]; methacrifos (1266); methamidophos (527); methidathion (529); methiocarb (530); methomyl (531); methyl bromide (537); metolcarb (550); mevinphos (556); mexacarbate (1290); milbemectin (557); milbemycin oxime (alternative name) [CCN]; mipafox (1293); monocrotophos (561); morphothion (1300); moxidectin (alternative name) [CCN]; naled (567); NC-184 (compound code); nifluridide (1309); nikkomycins (alternative name) [CCN]; nitrilacarb (1313); nitrilacarb 1:1 zinc chloride complex (1313); NNI-0101 (compound code); NNI-0250 (compound code); omethoate (594); oxamyl (602); oxydeprofos (1324); oxydisulfoton (1325); pp'-DDT (219); parathion (615); permethrin (626); petroleum oils (alternative name) (628); phenkapton (1330); phenthoate (631); phorate (636); phosalone (637); phosfolan (1338); phosmet (638); phosphamidon (639); phoxim (642); pirimiphos-methyl (652); polychloroterpenes (traditional name) (1347); polynactins (alternative name) (653); proclonol (1350); profenofos (662); promacyl (1354); propargite (671); propetamphos (673); propoxur (678); prothidathion (1360); prothoate (1362); pyrethrin I (696); pyrethrin II (696); pyrethrins (696); pyridaben (699); pyridaphenthion (701); pyrimidifen (706); pyrimitate (1370); quinalphos (711); quintiofos (1381); R-1492 (development code) (1382); RA-17 (development code) (1383); rotenone (722); schradan (1389); sebufos (alternative name); selamectin (alternative name) [CCN]; SI-0009 (compound code); sophamide (1402); spirodiclofen (738); spiromesifen (739); SSI-121 (development code) (1404); sulfiram (alternative name) [CCN]; sulfluramid (750); sulfotep (753); sulfur (754); SZI-121 (development code) (757); tau-fluvalinate (398); tebufenpyrad (763); TEPP (1417); terbam (alternative name); tetrachlorvinphos (777); tetradifon (786); tetranactin (alternative name) (653); tetrasul (1425); thiafenox (alternative name); thiocarboxime (1431); thiofanox (800); thiometon (801); thioquinox (1436); thuringiensin (alternative name) [CCN]; triamiphos (1441); triarathene (1443); triazophos (820); triazuron (alternative name); trichlorfon (824); trifenofos (1455); trinactin (alternative name) (653); vamidothion (847); vaniliprole [CCN]; YI-5302 (compound code); bethoxazin [CCN]; copper dioctanoate (IUPAC-Name) (170); copper sulfate (172); cybutryne [CCN]; dichlone (1052); dichlorophen (232); endothal (295); fentin (347); hydrated lime [CCN]; nabam (566); quinoclamine (714); quinonamid (1379); simazine (730); triphenyltin acetate (IUPAC-Name) (347); triphenyltin hydroxide (IUPAC-Name) (347); abamectin (1); crufomate (1011); doramectin (alternative name) [CCN]; emamectin (291); emamectin benzoate (291); eprinomectin (alternative name) [CCN]; ivermectin (alternative name) [CCN]; milbemycin oxime (alternative name) [CCN]; moxidectin (alternative name) [CCN]; piperazine [CCN]; selamectin (alternative name) [CCN]; spinosad (737); thiophanate (1435); chloralose (127); endrin (1122); fenthion (346); pyridin-4-amine (IUPAC-Name) (23); strychnine (745); 1-hydroxy-1H-pyridine-2-thione (IUPAC-Name) (1222); 4-(quinoxalin-2-ylamino)benzenesulfonamide (IUPAC-Name) (748); 8-hydroxyquinoline sulfate (446); bronopol (97); copper dioctanoate (IUPAC-Name) (170); copper hydroxide (IUPAC-Name) (169); cresol [CCN]; dichlorophen (232); dipyrithione (1105); dodicin (1112); fenaminosulf (1144); formaldehyde (404); hydrargaphen (alternative name) [CCN]; kasugamycin (483); kasugamycin hydrochloride hydrate (483); nickel bis(dimethyldithiocarbamate) (IUPAC-Name) (1308); nitrapyrin (580); octhilinone (590); oxolinic acid (606); oxytetracycline (611); potassium hydroxyquinoline sulfate (446); probenazole (658); streptomycin (744); streptomycin sesquisulfate (744); tecloftalam (766); thiomersal (alternative name) [CCN]; iodomethane (IUPAC-Name) (542); methyl bromide (537); apholate [CCN]; bisazir (alternative name) [CCN]; busulfan (alternative name) [CCN]; diflubenzuron (250); dimatif (alternative name) [CCN]; hemel [CCN]; hempa [CCN]; metepa [CCN]; methiotepa [CCN]; methyl apholate [CCN]; morzid [CCN]; penfluron (alternative name) [CCN]; tepa [CCN]; thiohempa (alternative name) [CCN]; thiotepa (alternative name) [CCN]; tretamine (alternative name) [CCN]; uredepa (alternative name) [CCN]; (E)-dec-5-en-1-yl acetate with (E)-dec-5-en-1-ol (IUPAC-Name) (222); (E)-tridec-4-en-1-yl acetate (IUPAC-Name) (829); (E)-6-methylhept-2-en-4-ol (IUPAC-Name) (541); (E,Z)-tetradeca-4,10-dien-1-yl acetate (IUPAC-Name) (779); (Z)-dodec-7-en-1-yl acetate (IUPAC-Name) (285); (Z)-hexadec-11-enal (IUPAC-Name) (436); (Z)-hexadec-11-en-1-yl acetate (IUPAC-Name) (437); (Z)-hexadec-13-en-11-yn-1-yl acetate (IUPAC-Name) (438); (Z)-icos-13-en-10-one (IUPAC-Name) (448); (Z)-tetradec-7-en-1-al (IUPAC-Name) (782); (Z)-tetradec-9-en-1-ol (IUPAC-Name) (783); (Z)-tetradec-9-en-1-yl acetate (IUPAC-Name) (784); (7E,9Z)-dodeca-7,9-dien-1-yl acetate (IUPAC-Name) (283); (9Z,11E)-tetradeca-9,11-dien-1-yl acetate (IUPAC-Name) (780); (9Z,12E)-tetradeca-9,12-dien-1-yl acetate (IUPAC-Name) (781); 14-methyloctadec-1-ene (IUPAC-Name) (545); 4-methylnonan-5-ol with 4-methylnonan-5-one (IUPAC-Name) (544); alpha-multistriatin (alternative name) [CCN]; brevicomin (alternative name) [CCN]; codlelure (alternative name) [CCN]; codlemone (alternative name) (167); cuelure (alternative name) (179); disparlure (277); dodec-8-en-1-yl acetate (IUPAC-Name) (286); dodec-9-en-1-yl acetate (IUPAC-Name) (287); dodeca-8,10-dien-1-yl acetate (IUPAC-Name) (284); dominicalure (alternative name) [CCN]; ethyl 4-methyloctanoate (IUPAC-Name) (317); eugenol (alternative name) [CCN]; frontalin (alternative name) [CCN]; gossyplure (alternative name) (420); grandlure (421); grandlure I (alternative name) (421); grandlure II (alternative name) (421); grandlure III (alternative name) (421); grandlure IV (alternative name) (421); hexalure [CCN]; ipsdienol (alternative name) [CCN]; ipsenol (alternative name) [CCN]; japonilure (alternative name) (481); lineatin (alternative name) [CCN]; litlure (alternative name) [CCN]; looplure (alternative name) [CCN]; medlure [CCN]; megatomoic acid (alternative name) [CCN]; methyl eugenol (alternative name) (540); muscalure (563); octadeca-2,13-dien-1-yl acetate (IUPAC-Name) (588); octadeca-3,13-dien-1-yl acetate (IUPAC-Name) (589); orfralure (alternative name) [CCN]; oryctalure (alternative name) (317); ostramone (alternative name) [CCN]; siglure [CCN]; sordidin (alternative name) (736); sulcatol (alternative name) [CCN]; tetradec-11-en-1-yl acetate (IUPAC-Name) (785); trimedlure (839); trimedlure A (alternative name) (839); trimedlure $B_1$ (alternative name) (839); trimedlure $B_2$ (alternative name) (839); trimedlure C (alternative name) (839); trunc-call (alternative name) [CCN]; 2-(octylthio) ethanol (IUPAC-Name) (591); butopyronoxyl (933); butoxy (polypropylene glycol) (936); dibutyl adipate (IUPAC-Name) (1046); dibutyl phthalate (1047); dibutyl succinate (IUPAC-Name) (1048); diethyltoluamide [CCN]; dimethyl carbate [CCN]; dimethyl phthalate [CCN]; ethyl hexanediol (1137); hexamide [CCN]; methoquin-butyl (1276); methylneodecanamide [CCN]; oxamate [CCN]; picaridin [CCN]; 1,1-dichloro-1-nitroethane (IUPAC-/Chemical Abstracts-Name) (1058); 1,1-dichloro-2,2-bis(4-ethylphenyl)ethane (IUPAC-Name) (1056); 1,2-dichloropropane (IUPAC-/Chemical Abstracts-Name) (1062); 1,2-dichloropropane with 1,3-dichloropropene (IUPAC-Name) (1063); 1-bromo-2-chloroethane (IUPAC-/Chemical Abstracts-Nalam) (916); 2,2,2-trichloro-1-(3,4-dichlorophenyl)ethyl acetate (IUPAC-Name) (1451); 2,2-dichlorovinyl 2-ethylsulfinylethyl methyl phosphate (IUPAC-Name) (1066); 2-(1,3-dithiolan-2-yl)phenyl dimethylcarbamate (IUPAC-/Chemical Abstracts-Name) (1109); 2-(2-butoxyethoxy)ethyl thiocyanate (IUPAC-/Chemical Abstracts-Name) (935); 2-(4,5-dimethyl-1,3-dioxolan-2-yl)phenyl methylcarbamate (IUPAC-/Chemical Abstracts-Name) (1084); 2-(4-chloro-3,5-xylyloxy)ethanol (IUPAC-Name) (986); 2-chlorovinyl diethyl phosphate (IUPAC-Name) (984); 2-imidazolidone (IUPAC-Name) (1225); 2-isovalerylindan-1,3-dione (IUPAC-Name) (1246); 2-methyl(prop-2-ynyl)aminophenyl methylcarbamate (IUPAC-Name) (1284); 2-thiocyanatoethyl laurate (IUPAC-Name) (1433); 3-bromo-1-chloroprop-1-ene (IUPAC-Name) (917); 3-methyl-1-phenylpyrazol-5-yl dimethylcarbamate (IUPAC-Name) (1283); 4-methyl(prop-2-ynyl)amino-3,5-xylyl methyl-carbamate (IUPAC-Name) (1285); 5,5-dimethyl-3-oxocyclohex-1-enyl dimethylcarbamate (IUPAC-Name) (1085); abamectin (1); acephate (2); acetamiprid (4); acethion (alternative name) [CCN]; acetoprole [CCN]; acrinathrin (9); acrylonitrile (IUPAC-Name) (861); alanycarb (15); aldicarb (16); aldoxycarb (863); aldrin (864); allethrin (17); allosamidin (alternative name) [CCN]; allyxycarb (866); alpha-cypermethrin (202); alpha-ecdysone (alternative name) [CCN]; aluminium phosphide (640); amidithion (870); amidothioate (872); aminocarb (873); amiton (875); amiton hydrogen oxalate (875); amitraz (24); anabasine (877); athidathion (883); AVI 382 (compound code); AZ 60541 (compound code); azadirachtin (alternative name) (41); azamethiphos (42); azinphos-ethyl (44); azinphos-methyl (45); azothoate (889); *Bacillus thuringiensis* delta endotoxins (alternative name) (52); barium hexafluorosilicate (alternative name) [CCN]; barium polysulfide (IUPAC-/Chemical Abstracts-Name) (892); barthrin [CCN]; BAS 320 I (compound code); Bayer 22/190 (development code) (893); Bayer 22408 (development code) (894); bendiocarb (58); benfuracarb (60); bensultap (66); beta-cyfluthrin (194); beta-cypermethrin (203); bifenthrin (76); bioallethrin (78); bioallethrin S-cyclopentenyl isomer (alternative name) (79); bioethanomethrin [CCN]; biopermethrin (908); bioresmethrin (80); bis(2-chloroethyl) ether (IUPAC-Name) (909); bistrifluron (83); borax (86); brofenvalerate (alternative name); bromfenvinfos (914); bromocyclen (918); bromo-DDT (alternative name) [CCN]; bromophos (920); bromophos-ethyl (921); bufencarb (924); buprofezin (99); butacarb (926); butathiofos (927); butocarboxim (103); butonate (932); butoxycarboxim (104); butylpyridaben (alternative name); cadusafos (109); calcium arsenate [CCN]; calcium cyanide (444); calcium polysulfide (IUPAC-Name) (111); camphechlor (941); carbanolate (943); carbaryl (115); carbofuran (118); carbon disulfide (IUPAC-/Chemical Abstracts-Name) (945); carbon tetrachloride (IUPAC-Name) (946); carbophenothion (947); carbosulfan (119); cartap (123); cartap hydrochloride (123); cevadine (alternative name) (725); chlorbicyclen (960); chlordane (128); chlordecone (963); chlordimeform (964); chlordimeform hydrochloride (964); chlorethoxyfos (129); chlorfenapyr (130); chlorfenvinphos (131); chlorfluazuron (132); chlormephos (136); chloroform [CCN]; chloropicrin (141); chlorphoxim (989); chlorprazophos (990); chlorpyrifos (145); chlorpyrifos-methyl (146); chlorthiophos (994); chromafenozide (150); cinerin I (696); cinerin II (696); cinerins (696); cis-resmethrin (alternative name); cismethrin (80); clocythrin (alternative name); cloethocarb (999); closantel (alternative name) [CCN]; clothianidin (165); copper acetoarsenite [CCN]; copper arsenate [CCN]; copper oleate [CCN]; coumaphos (174); coumithoate (1006); crotamiton (alternative name) [CCN]; crotoxyphos (1010); crufomate (1011); cryolite (alternative name) (177); CS 708 (development code) (1012); cyanofenphos (1019); cyanophos (184); cyanthoate (1020); cyclethrin [CCN]; cycloprothrin (188); cyfluthrin (193); cyhalothrin (196); cypermethrin (201); cyphenothrin (206); cyromazine (209); cythioate (alternative name) [CCN]; d-limonene (alternative name) [CCN]; d-tetramethrin (alternative name) (788); DAEP (1031); dazomet (216); DDT (219); decarbofuran (1034); deltamethrin (223); demephion (1037); demephion-O (1037); demephion-S (1037); demeton (1038); demeton-methyl (224); demeton-O (1038); demeton-O-methyl (224); demeton-S (1038); demeton-S-methyl (224); demeton-S-methylsulphon (1039); diafenthiuron (226); dialifos (1042); diamidafos (1044); diazinon (227); dicapthon (1050); dichlofenthion (1051); dichlorvos (236); diclipos (alternative name); dicresyl (alternative name) [CCN]; dicrotophos (243); dicyclanil (244); dieldrin (1070); diethyl 5-methylpyrazol-3-yl phosphate (IUPAC-Name) (1076); diflubenzuron (250); dilor (alternative name) [CCN]; dimefluthrin [CCN]; dimefox (1081); dimetan (1085); dimethoate (262); dimethrin (1083); dimethylvinphos (265); dimetilan (1086); dinex (1089); dinex-diclexine (1089); dinoprop (1093); dinosam (1094); dinoseb (1095); dinotefuran (271); diofenolan (1099); dioxabenzofos (1100); dioxacarb (1101); dioxathion (1102); disulfoton (278); dithicrofos (1108); DNOC (282); doramectin (alternative name) [CCN]; DSP (1115); ecdysterone (alternative name) [CCN]; E1 1642 (development code) (1118); emamectin (291); emamectin benzoate (291); EMPC (1120); empenthrin (292); endosulfan (294); endothion (1121); endrin (1122); EPBP (1123); EPN (297); epofenonane (1124); eprinomectin (alternative name) [CCN]; esfenvalerate (302); etaphos (alternative name) [CCN]; ethiofencarb (308); ethion (309); ethiprole (310); ethoate-methyl (1134); ethoprophos (312); ethyl formate (IUPAC-Name) [CCN]; ethyl-DDD (alternative name) (1056); ethylene dibromide (316); ethylene dichloride (chemical name) (1136); ethylene oxide [CCN]; etofenprox (319); etrimfos (1142); EXD (1143); famphur (323); fenamiphos (326); fenazaflor (1147); fenchlorphos (1148); fenethacarb (1149); fenfluthrin (1150); fenitrothion (335); fenobucarb (336); fenoxacrim (1153); fenoxycarb (340); fenpirithrin (1155); fenpropathrin (342); fenpyrad (alternative name); fensulfothion (1158); fenthion (346); fenthion-ethyl [CCN]; fenvalerate (349); fipronil (354); flonicamid (358); flucofuron (1168); flucycloxuron (366); flucythrinate (367); fluenetil (1169); flufenerim [CCN]; flufenoxuron (370); flufenprox (1171); flumethrin (372); fluvalinate (1184); FMC 1137 (development code) (1185); fonofos (1191); formetanate (405); formetanate hydrochloride (405); formothion (1192); formparanate (1193); fosmethilan (1194); fospirate (1195); fosthiazate (408); fosthietan (1196); furathiocarb (412); furethrin (1200); gamma-cyhalothrin (197); gamma-HCH (430); guazatine (422); guazatine acetates (422); GY-81 (development code) (423); halfenprox (424); halofenozide (425); HCH (430); HEOD (1070); heptachlor (1211); heptenophos (432); heterophos [CCN]; hexaflumuron (439); HHDN (864); hydramethylnon (443); hydrogen cyanide (444); hydroprene (445); hyquincarb (1223); imidacloprid (458); imiprothrin (460); indoxacarb (465); iodomethane (IUPAC-Name) (542); IPSP (1229); isazofos (1231); isobenzan (1232); isocarbophos (alternative name) (473); isodrin (1235); isofenphos (1236); isolane (1237); isoprocarb (472); isopropyl O-(methoxyaminothiophosphoryl)salicylate (IUPAC-Name) (473); isoprothiolane (474); isothioate (1244); isoxathion (480); ivermectin (alternative name) [CCN]; jasmolin I (696); jasmolin II (696); jodfenphos (1248); juvenile hormone I (alternative name) [CCN]; juvenile hormone II (alternative name) [CCN]; juvenile hormone III (alternative name) [CCN]; kelevan (1249); kinoprene (484); lambda-cyhalothrin (198); lead arsenate [CCN]; leptophos (1250); lindane (430); lirimfos (1251); lufenuron (490); lythidathion (1253); m-cumenyl methylcarbamate (IUPAC-Name) (1014); magnesium phosphide (IUPAC-Name) (640); malathion (492); malonoben (1254); mazidox (1255); mecarbam (502); mecarphon (1258); menazon (1260); mephosfolan (1261); mercurous chloride (513); mesulfenfos (1263); metam (519); metam-potassium (alternative name) (519); metam-sodium (519); methacrifos (1266); methamidophos (527); methanesulfonyl fluoride (IUPAC-/Chemical Abstracts-Name) (1268); methidathion (529); methiocarb (530); methocrotophos (1273); methomyl (531); methoprene (532); methoquin-butyl (1276); methothrin (alternative name) (533); methoxychlor (534); methoxyfenozide (535); methyl bromide (537); methyl isothiocyanate (543); methylchloroform (alternative name) [CCN]; methylene chloride [CCN]; metofluthrin [CCN]; metolcarb (550); metoxadiazone (1288); mevinphos (556); mexacarbate (1290); milbemectin (557); milbemycin oxime (alternative name) [CCN]; mipafox (1293); mirex (1294); monocrotophos (561); morphothion (1300); moxidectin (alternative name) [CCN]; naftalofos (alternative name) [CCN]; naled (567); naphthalene (IUPAC-/Chemical Abstracts-Name) (1303); NC-170 (development code) (1306); NC-184 (compound code); nicotine (578); nicotine sulfate (578); nifluridide (1309); nitenpyram (579); nithiazine (1311); nitrilacarb (1313); nitrilacarb 1:1 zinc chloride complex (1313); NNI-0101 (compound code); NNI-0250 (compound code); nornicotine (traditional name) (1319); novaluron (585); noviflumuron (586); O-2,5-dichloro-4-iodophenyl O-ethyl ethylphosphonothioate (IUPAC-Name) (1057); O,O-diethyl O-4-methyl-2-oxo-2H-chromen-7-yl phosphorothioate (IUPAC-Name) (1074); O,O-diethyl O-6-methyl-2-propylpyrimidin-4-yl phosphorothioate (IUPAC-Name) (1075); O,O,O',O'-tetrapropyl dithiopyrophosphate (IUPAC-Name) (1424); oleic acid (IUPAC-Name) (593); omethoate (594); oxamyl (602); oxydemeton-methyl (609); oxydeprofos (1324); oxydisulfoton (1325); pp'-DDT (219); para-dichlorobenzene [CCN]; parathion (615); parathion-methyl (616); penfluron (alternative name) [CCN]; pentachlorophenol (623); pentachlorophenyl laurate (IUPAC-Name) (623); permethrin (626); petroleum oils (alternative name) (628); PH 60-38 (development code) (1328); phenkapton (1330); phenothrin (630); phenthoate (631); phorate (636); phosalone (637); phosfolan (1338); phosmet (638); phosnichlor (1339); phosphamidon (639); phosphine (IUPAC-Name) (640); phoxim (642); phoxim-methyl (1340); pirimetaphos (1344); pirimicarb (651); pirimiphos-ethyl (1345); pirimiphos-methyl (652); polychlorodicyclopentadiene isomers (IUPAC-Name) (1346); polychloroterpenes (traditional name) (1347); potassium arsenite [CCN]; potassium thiocyanate [CCN]; prallethrin (655); precocene I (alternative name) [CCN]; precocene II (alternative name) [CCN]; precocene III (alternative name) [CCN]; primidophos (1349); profenofos (662); profluthrin [CCN]; promacyl (1354); promecarb (1355); propaphos (1356); propetamphos (673); propoxur (678); prothidathion (1360); prothiofos (686); prothoate (1362); protrifenbute [CCN]; pymetrozine (688); pyraclofos (689); pyrazophos (693); pyresmethrin (1367); pyrethrin I (696); pyrethrin II (696); pyrethrins (696); pyridaben (699); pyridalyl (700); pyridaphenthion (701); pyrimidifen (706); pyrimitate (1370); pyriproxyfen (708); quassia (alternative name) [CCN]; quinalphos (711); quinalphos-methyl (1376); quinothion (1380); quintiofos (1381); R-1492 (development code) (1382); rafoxanide (alternative name) [CCN]; resmethrin (719); rotenone (722); RU 15525 (development code) (723); RU 25475 (development code) (1386); ryania (alternative name) (1387); ryanodine (traditional name) (1387); sabadilla (alternative name) (725); schradan (1389); sebufos (alternative name); selamectin (alternative name)

[CCN]; SI-0009 (compound code); silafluofen (728); SN 72129 (development code) (1397); sodium arsenite [CCN]; sodium cyanide (444); sodium fluoride (IUPAC-/Chemical Abstracts-Name) (1399); sodium hexafluorosilicate (1400); sodium pentachlorophenoxide (623); sodium selenate (IUPAC-Name) (1401); sodium thiocyanate [CCN]; sophamide (1402); spinosad (737); spiromesifen (739); sulcofuron (746); sulcofuron-sodium (746); sulfluramid (750); sulfotep (753); sulfuryl fluoride (756); sulprofos (1408); tar oils (alternative name) (758); tau-fluvalinate (398); tazimcarb (1412); TDE (1414); tebufenozide (762); tebufenpyrad (763); tebupirimfos (764); teflubenzuron (768); tefluthrin (769); temephos (770); TEPP (1417); terallethrin (1418); terbam (alternative name); terbufos (773); tetrachloroethane [CCN]; tetrachlorvinphos (777); tetramethrin (787); theta-cypermethrin (204); thiacloprid (791); thiafenox (alternative name); thiamethoxam (792); thicrofos (1428); thiocarboxime (1431); thiocyclam (798); thiocyclam hydrogen oxalate (798); thiodicarb (799); thiofanox (800); thiometon (801); thionazin (1434); thiosultap (803); thiosultap-sodium (803); thuringiensin (alternative name) [CCN]; tolfenpyrad (809); tralomethrin (812); transfluthrin (813); transpermethrin (1440); triamiphos (1441); triazamate (818); triazophos (820); triazuron (alternative name); trichlorfon (824); trichlormetaphos-3 (alternative name) [CCN]; trichloronat (1452); trifenofos (1455); triflumuron (835); trimethacarb (840); triprene (1459); vamidothion (847); vaniliprole [CCN]; veratridine (alternative name) (725); veratrine (alternative name) (725); XMC (853); xylylcarb (854); YI-5302 (compound code); zeta-cypermethrin (205); zetamethrin (alternative name); zinc phosphide (640); zolaprofos (1469) and ZXI 8901 (development code) (858); a compound of formula A-1

(A-1)

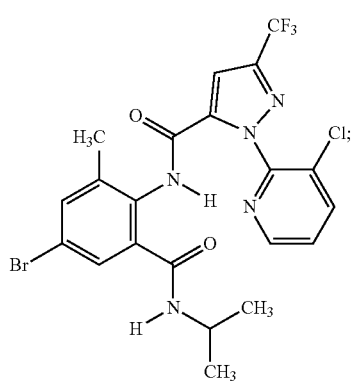

a compound of formula A-2

(A-2)

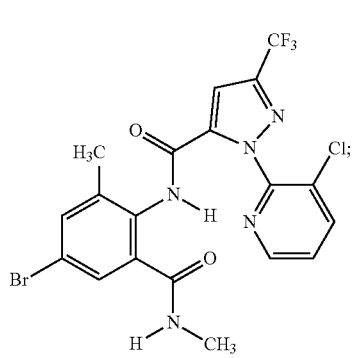

a compound of formula A-3

(A-3)

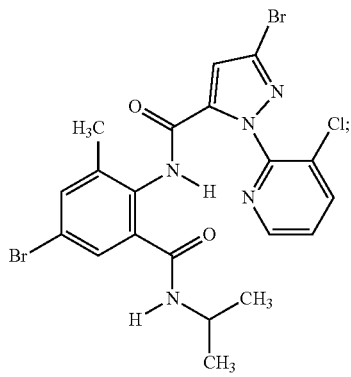

a compound of formula A-4

(A-4)

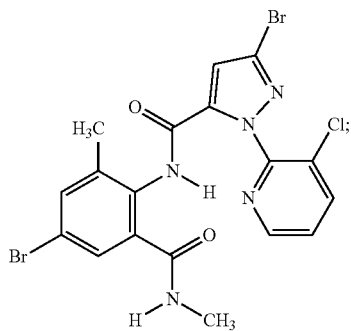

a compound of formula A-5

(A-5)

a compound of formula A-6

(A-6)

a compound of formula A-7
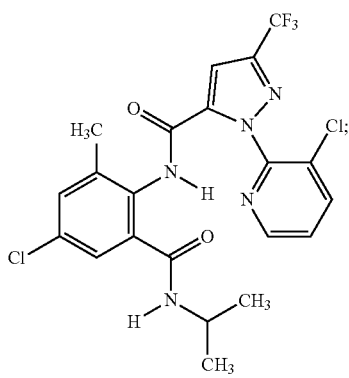
a compound of formula A-8
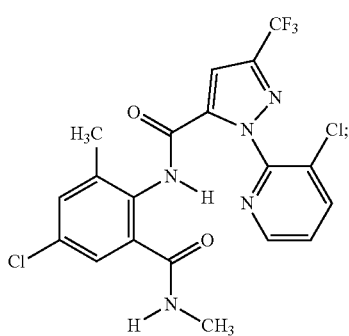
a compound of formula A-9
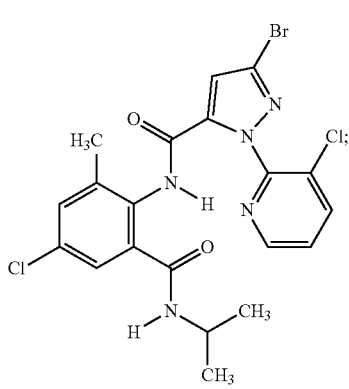
a compound of formula A-10
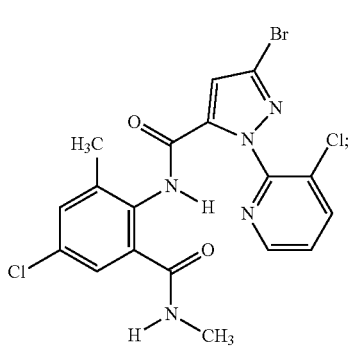
a compound of formula A-11
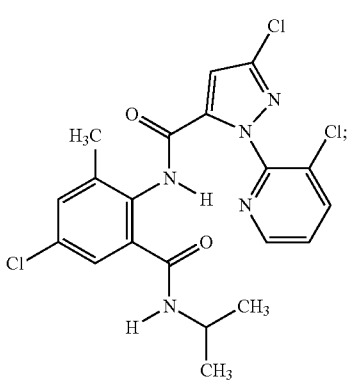
a compound of formula A-12
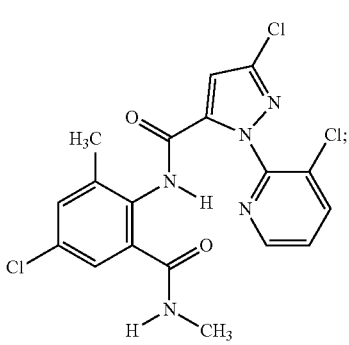
a compound of formula A-13
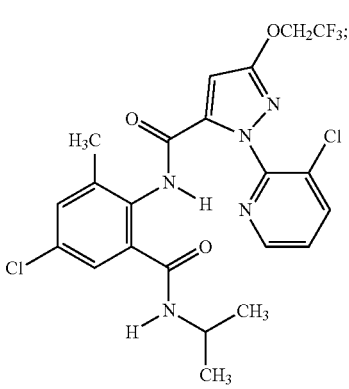
a compound of formula A-14
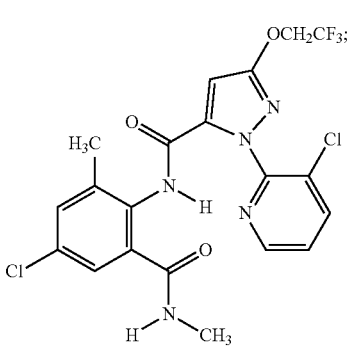

a compound of formula A-15
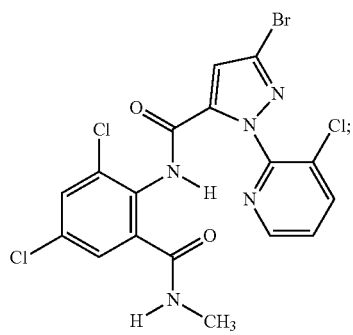
a compound of formula A-15A
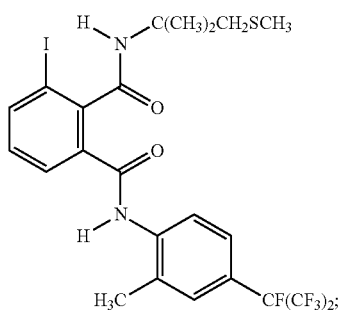
a compound of formula (A-16)
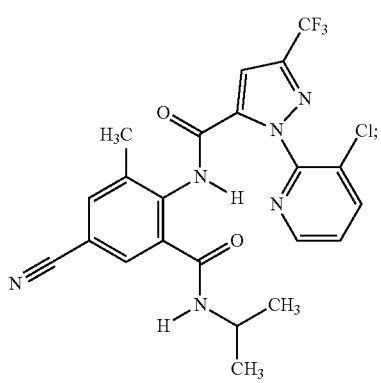
a compound of formula (A-17)
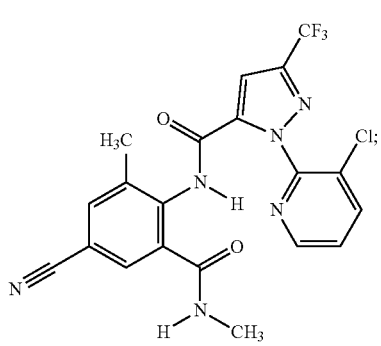
a compound of formula (A-18)
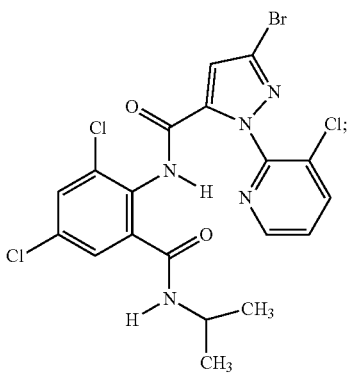
a compound of formula (A-19)
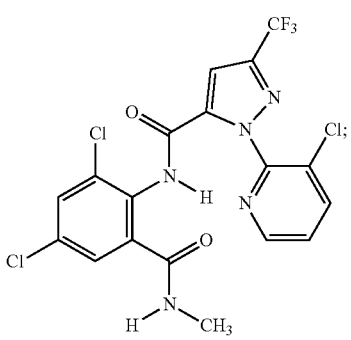
a compound of formula (A-20)
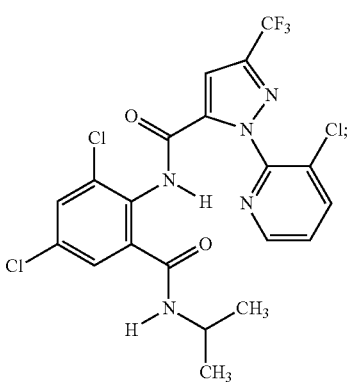

a compound of formula (A-21)

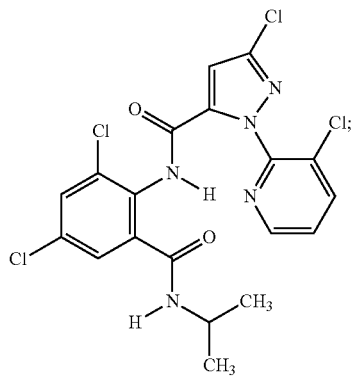

a compound of formula (A-22)

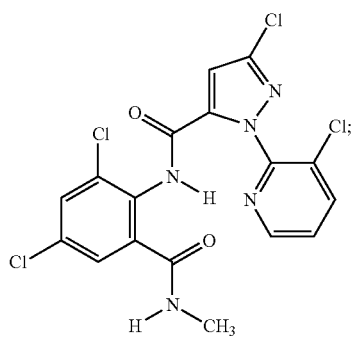

a compound of formula (A-23)

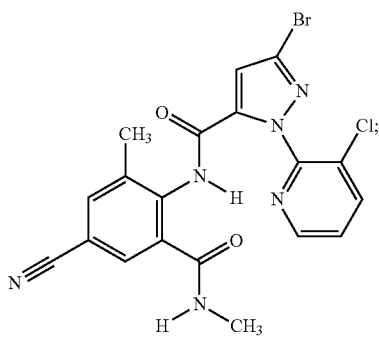

a compound of formula (A-24)

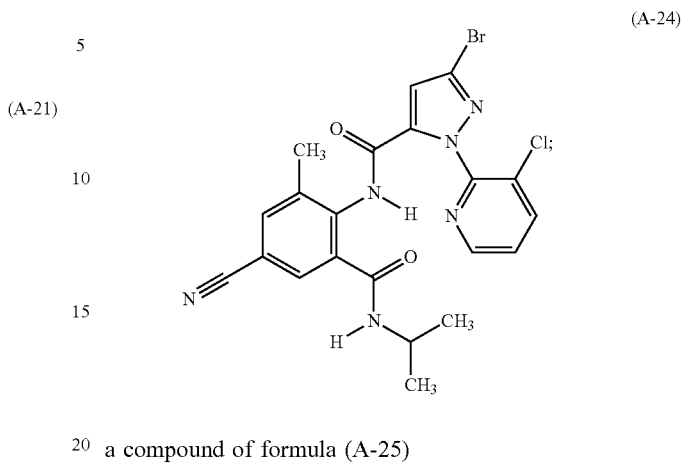

a compound of formula (A-25)

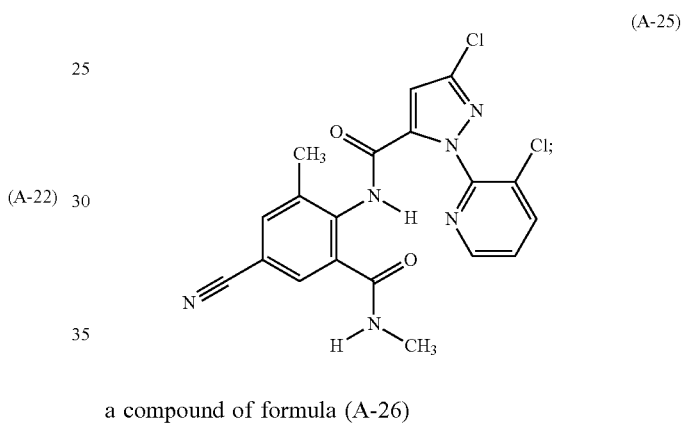

a compound of formula (A-26)

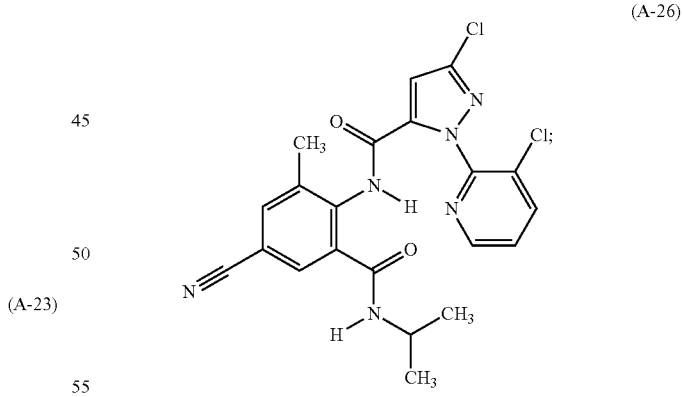

bis(tributyltin) oxide (IUPAC-Name) (913); bromoacetamide [CCN]; calcium arsenate [CCN]; cloethocarb (999); copper acetoarsenite [CCN]; copper sulfate (172); fentin (347); ferric phosphate (IUPAC-Name) (352); metaldehyde (518); methiocarb (530); niclosamide (576); niclosamideolamine (576); pentachlorophenol (623); sodium pentachlorophenoxide (623); tazimcarb (1412); thiodicarb (799); tributyltin oxide (913); trifenmorph (1454); trimethacarb (840); triphenyltin acetate (IUPAC-Name) (347); triphenyltin hydroxide (IUPAC-Name) (347); 1,2-dibromo-3-chloropropane (IUPAC-/Chemical Abstracts-Name) (1045); 1,2-dichloropropane (IUPAC-/Chemical Abstracts-Name)

(1062); 1,2-dichloropropane with 1,3-dichloropropene (IU-PAC-Name) (1063); 1,3-dichloropropene (233); 3,4-dichlorotetrahydrothiophene 1,1-dioxide (IUPAC-/Chemical Abstracts-Name) (1065); 3-(4-chlorophenyl)-5-methylrhodanine (IUPAC-Name) (980); 5-methyl-6-thioxo-1,3,5-thiadiazinan-3-ylacetic acid (IUPAC-Name) (1286); 6-isopentenylaminopurine (alternative name) (210); abamectin (1); acetoprole [CCN]; alanycarb (15); aldicarb (16); aldoxycarb (863); AZ 60541 (compound code); benclothiaz [CCN]; benomyl (62); butylpyridaben (alternative name); cadusafos (109); carbofuran (118); carbon disulfide (945); carbosulfan (119); chloropicrin (141); chlorpyrifos (145); cloethocarb (999); cytokinins (alternative name) (210); dazomet (216); DBCP (1045); DCIP (218); diamidafos (1044); dichlofenthion (1051); dicliphos (alternative name); dimethoate (262); doramectin (alternative name) [CCN]; emamectin (291); emamectin benzoate (291); eprinomectin (alternative name) [CCN]; ethoprophos (312); ethylene dibromide (316); fenamiphos (326); fenpyrad (alternative name); fensulfothion (1158); fosthiazate (408); fosthietan (1196); furfural (alternative name) [CCN]; GY-81 (development code) (423); heterophos [CCN]; iodomethane (IUPAC-Name) (542); isamidofos (1230); isazofos (1231); ivermectin (alternative name) [CCN]; kinetin (alternative name) (210); mecarphon (1258); metam (519); metam-potassium (alternative name) (519); metam-sodium (519); methyl bromide (537); methyl isothiocyanate (543); milbemycin oxime (alternative name) [CCN]; moxidectin (alternative name) [CCN]; *Myrothecium verrucaria* composition (alternative name) (565); NC-184 (compound code); oxamyl (602); phorate (636); phosphamidon (639); phosphocarb [CCN]; sebufos (alternative name); selamectin (alternative name) [CCN]; spinosad (737); terbam (alternative name); terbufos (773); tetrachlorothiophene (IUPAC-/Chemical Abstracts-Name) (1422); thiafenox (alternative name); thionazin (1434); triazophos (820); triazuron (alternative name); xylenols [CCN]; YI-5302 (compound code); zeatin (alternative name) (210); potassium ethylxanthate [CCN]; nitrapyrin (580); acibenzolar (6); acibenzolar-S-methyl (6); probenazole (658); *Reynoutria sachalinensis* extract (alternative name) (720); 2-isovalerylindan-1,3-dione (IUPAC-Name) (1246); 4-(quinoxalin-2-ylamino)benzenesulfonamide (IUPAC-Name) (748); alpha-chlorohydrin [CCN]; aluminium phosphide (640); antu (880); arsenous oxide (882); barium carbonate (891); bisthiosemi (912); brodifacoum (89); bromadiolone (91); bromethalin (92); calcium cyanide (444); chloralose (127); chlorophacinone (140); cholecalciferol (alternative name) (850); coumachlor (1004); coumafuryl (1005); coumatetralyl (175); crimidine (1009); difenacoum (246); difethialone (249); diphacinone (273); ergocalciferol (301); flocoumafen (357); fluoroacetamide (379); flupropadine (1183); flupropadine hydrochloride (1183); gamma-HCH (430); HCH (430); hydrogen cyanide (444); iodomethane (IUPAC-Name) (542); lindane (430); magnesium phosphide (IUPAC-Name) (640); methyl bromide (537); norbormide (1318); phosacetim (1336); phosphine (IUPAC-Name) (640); phosphorus [CCN]; pindone (1341); potassium arsenite [CCN]; pyrinuron (1371); scilliroside (1390); sodium arsenite [CCN]; sodium cyanide (444); sodium fluoroacetate (735); strychnine (745); thallium sulfate [CCN]; warfarin (851); zinc phosphide (640); 2-(2-butoxyethoxy)ethyl piperonylate (IUPAC-Name) (934); 5-(1,3-benzodioxol-5-yl)-3-hexylcyclohex-2-enone (IUPAC-Name) (903); farnesol with nerolidol (alternative name) (324); MB-599 (development code) (498); MGK 264 (development code) (296); piperonyl butoxide (649); piprotal (1343); propyl isome (1358); S421 (development code) (724); sesamex (1393); sesasmolin (1394); sulfoxide (1406); anthraquinone (32); chloralose (127); copper naphthenate [CCN]; copper oxychloride (171); diazinon (227); dicyclopentadiene (chemical name) (1069); guazatine (422); guazatine acetates (422); methiocarb (530); pyridin-4-amine (IU-PAC-Name) (23); thiram (804); trimethacarb (840); zinc naphthenate [CCN]; ziram (856); imanin (alternative name) [CCN]; ribavirin (alternative name) [CCN]; mercuric oxide (512); octhilinone (590); thiophanate-methyl (802); a compound of formula F-1

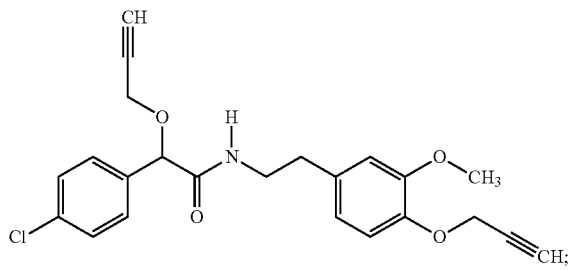

a compound of formula F-2A

wherein R' is hydrogen, $C_{1-4}$alkyl or $C_{1-4}$haloalkyl;
a compound of formula F-3

(F-3)

a compound of formula F-4

(F-4)

a compound of formula F-5

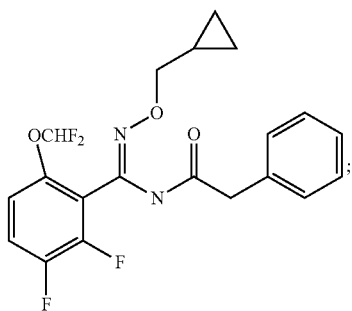
(F-5)

a compound of formula F-6

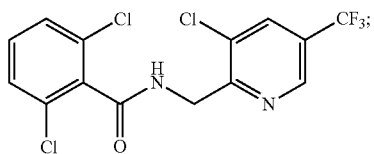
(F-6)

a compound of formula F-7

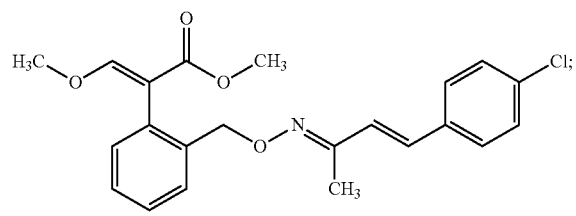
(F-7)

and a compound of formula F-8

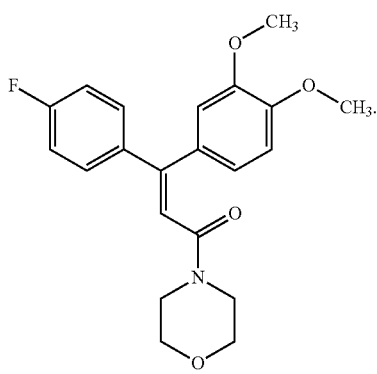
(F-8)

It has now been found, surprisingly, that the active ingredient mixture according to the invention not only brings about the additive enhancement of the spectrum of action with respect to the phytopathogen to be controlled that was in principle to be expected but achieves a synergistic effect which extends the range of action of the component (A) and of the component (B) in two ways. Firstly, the rates of application of the component (A) and of the component (B) are lowered whilst the action remains equally good. Secondly, the active ingredient mixture still achieves a high degree of phytopathogen control even where the two individual components have become totally ineffective in such a low application rate range. This allows, on the one hand, a substantial broadening of the spectrum of phytopathogens that can be controlled and, on the other hand, increased safety in use.

However, besides the actual synergistic action with respect to fungicidal activity, the pesticidal compositions according to the invention also have further surprising advantageous properties which can also be described, in a wider sense, as synergistic activity. Examples of such advantageous properties that may be mentioned are: a broadening of the spectrum of fungicidal activity to other phytopathogens, for example to resistant strains; a reduction in the rate of application of the active ingredients; synergistic activity against animal pests, such as insects or representatives of the order Acarina; a broadening of the spectrum of pesticidal activity to other animal pests, for example to resistant animal pests; adequate pest control with the aid of the compositions according to the invention, even at a rate of application at which the individual compounds are totally ineffective; advantageous behaviour during formulation and/or upon application, for example upon grinding, sieving, emulsifying, dissolving or dispensing; increased storage stability; improved stability to light; more advantageuos degradability; improved toxicological and/or ecotoxicological behaviour; improved characteristics of the useful plants including: emergence, crop yields, more developed root system, tillering increase, increase in plant height, bigger leaf blade, less dead basal leaves, stronger tillers, greener leaf color, less fertilizers nedded, less seeds needed, more productive tillers, earlier flowering, early grain maturity, less plant verse (lodging), increased shoot growth, improved plant vigor, and early germination; or any other advantages familiar to a person skilled in the art.

The compounds of formula I occur in different stereoisomeric forms, which are described in formulae $I_I$, $I_{II}$, $I_{III}$ and $I_{IV}$:

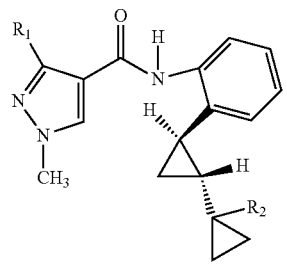
$I_I$

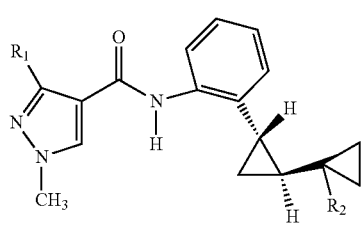
$I_{II}$

-continued

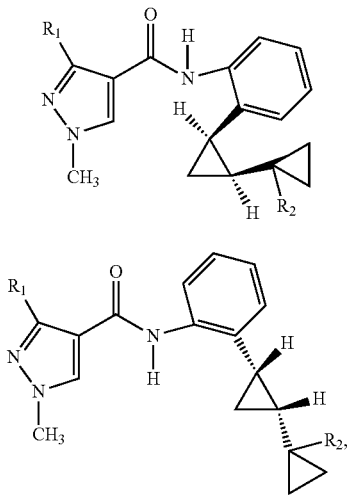

$I_{III}$

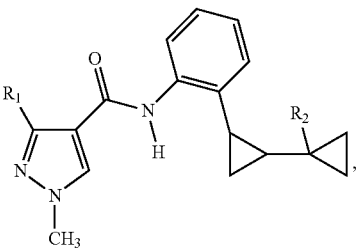

$I_{IV}$ wherein $R_1$ and $R_2$ are as defined under formula I. The invention covers all such stereoisomers and mixtures thereof in any ratio.

The compounds of formula I and their manufacturing processes starting from known and commercially available compounds are described in WO 03/074491. In particular it is described in WO 03/074491 that a compound of formula I

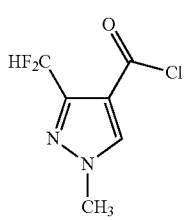
(I)

wherein $R_1$ is difluoromethyl and $R_2$ is hydrogen can be prepared by reacting an acid chloride of formula II

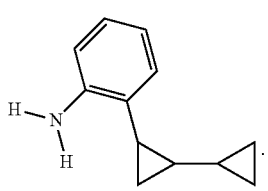
(II)

with an amine of formula III (III)

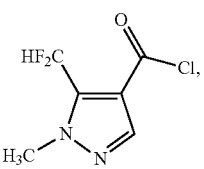

Acids of formula IV

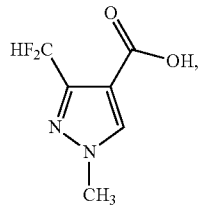
(IV)

are used for the production of the acid chlorides of formula II, via reaction steps as described in WO 03/074491. When producing the acids of the formula IV using said methology impurities of formula IVA, IVB and/or IVC may be formed:

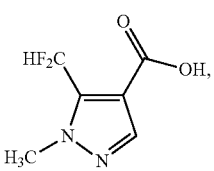
(IVA)

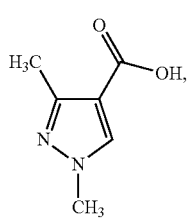
(IVB)

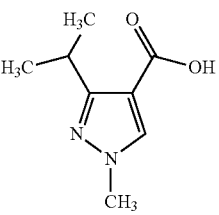
(IVC)

When applying the described manufacturing processes for compounds of formula I some/all of those impurities may be carried through different steps of said manufacturing processes. This then can lead to the formation of the corresponding acid chlorides (IIA, IIB and/or IIC)

(IIA)

(IIB)

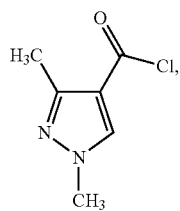

(III)

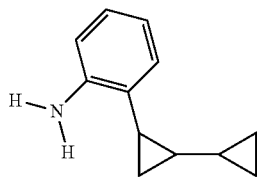

starting from known and commercially available compounds. A step in said process is the reaction of a compound of formula VI (IIC)

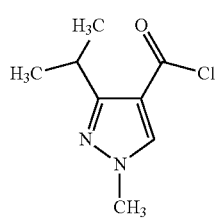

(VI)

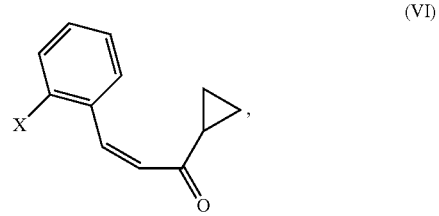

and to the formation of the corresponding amides (VA, VB and/or VC)

wherein X is halogen, with hydrazine hydrate in a solvent. During this step a compound of formula VII (VA)

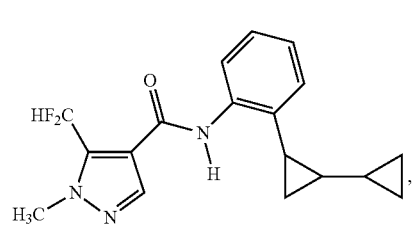

(VII)

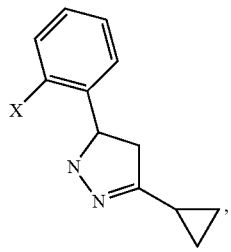

(VB)

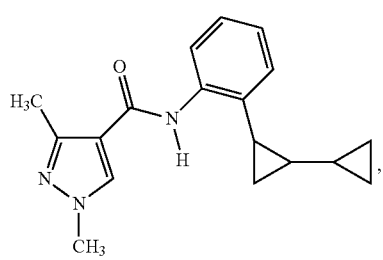

wherein X is halogen, is formed. Preferred compounds of formula VII are compounds, wherein X is chloride or bromide. Said preferred compounds of formula VII can be used advantageously for the production of amines of formula III using methods as described in WO 03/074491.

Using said processes described in WO 03/074491 for the manufacture of the amines of formula III, the following impurities of formula VIIIA, VIIIB, VIIIC and/or VIIID may be formed:

(VC)

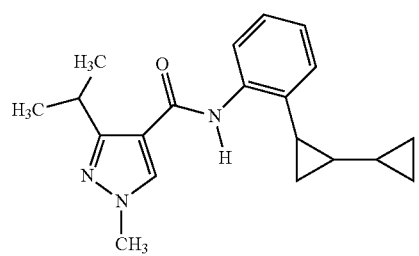

(VIIIA)

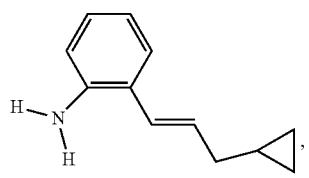

as further impurities of compounds of formula I, wherein $R_1$ is difluoromethyl and $R_2$ is hydrogen. The presence/amount of said impurities in preparations of said compounds of formula I varies dependent on purification steps used.

WO 03/074491 describes on page 20 of the specification a process for the manufacture of amines of formula III (VIIIB)

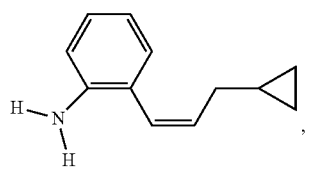

(VIIIC)
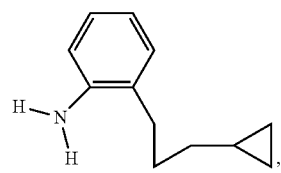
(VIIID)
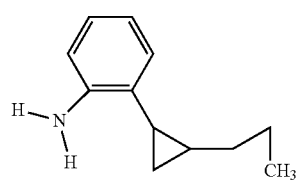
When applying the described manufacturing processes for compounds of formula I some/all of those impurities may be carried through different steps of said manufacturing processes. This then can lead to the formation of the corresponding amides (IXA, IXB, IXC, IXD, IXE, IXF, IXG, IXH, IXI, IXJ, IXK and/or IXL)
(IXA)
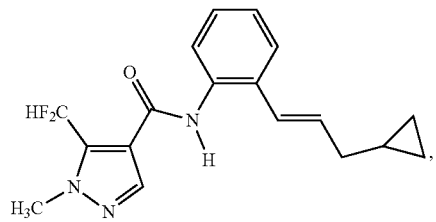
(IXB)
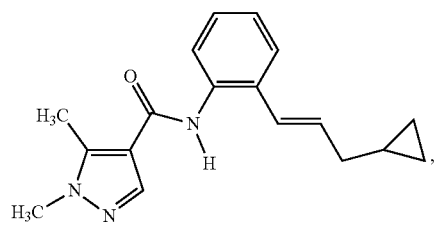
(IXC)
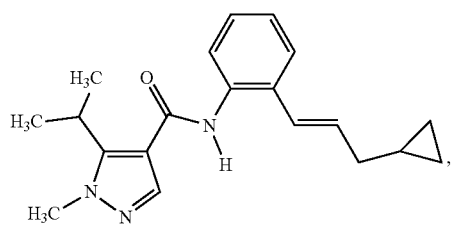
(IXD)
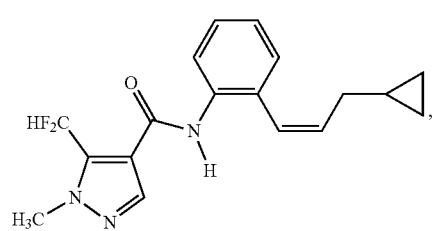
(IXE)
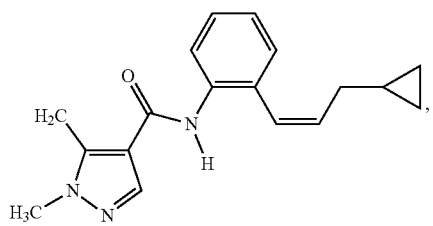
(IXF)
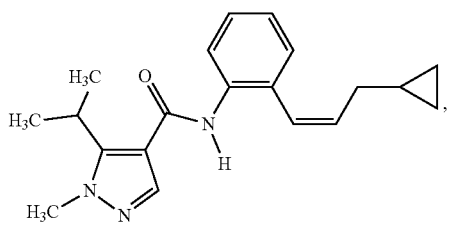
(IXG)
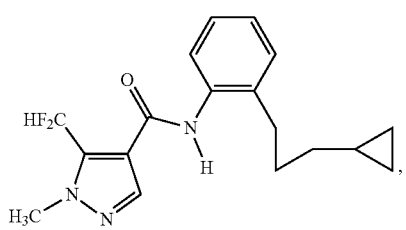
(IXH)
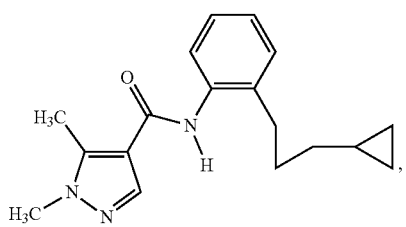
(IXI)
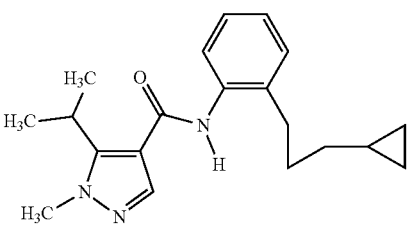
(IXJ)
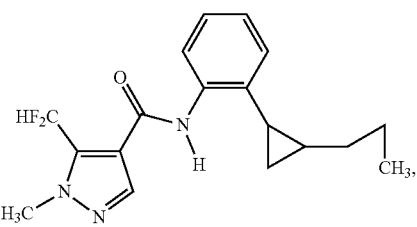
(IXK)
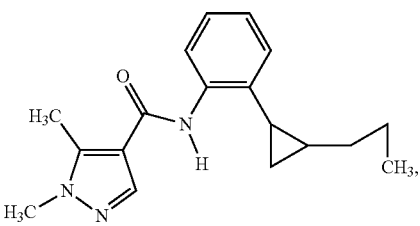

-continued

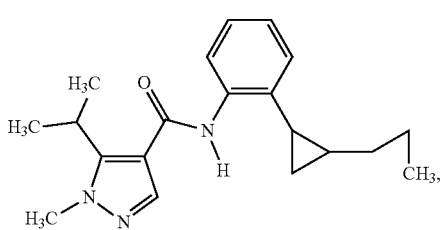

(IXL)

as further impurities of compounds of formula I, wherein $R_1$ is difluoromethyl and $R_2$ is hydrogen. The presence/amount of said impurities in preparations of said compounds of formula I varies dependent on purification steps used.

The components (B) are known. Where the components (B) are included in "The Pesticide Manual" [The Pesticide Manual—A World Compendium; Thirteenth Edition; Editor: C. D. S. Tomlin; The British Crop Protection Council], they are described therein under the entry number given in round brackets hereinabove for the particular component (B); for example, the compound "abamectin" is described under entry number (1). Where "[CCN]" is added hereinabove to the particular component (B), the component (B) in question is included in the "Compendium of Pesticide Common Names", which is accessible on the internet [A. Wood; Compendium of Pesticide Common Names, Copyright© 1995-2004]; for example, the compound "acetoprole" is described under the internet address http://www.alanwood.net/pesticides/acetoprole.html.

Most of the components (B) are referred to hereinabove by a so-called "common name", the relevant "ISO common name" or another "common name" being used in individual cases. If the designation is not a "common name", the nature of the designation used instead is given in round brackets for the particular component (B); in that case, the IUPAC name, the IUPAC/Chemical Abstracts name, a "chemical name", a "traditional name", a "compound name" or a "develoment code" is used or, if neither one of those designations nor a "common name" is used, an "alternative name" is employed.

The following components B) are registered under a CAS-Reg. No. http://www/: Aldimorph (CAS 91315-15-0); Iodocarb (3-Iodo-2-propynyl butyl carbamate) (CAS 55406-53-6); Fentin chloride (CAS 668-34-8); Hymexazole (CAS 10004-44-1); Phosphoric acid (CAS 7664-38-2); Tecloftalam (CAS 76280-91-6); Arsenates (CAS 1327-53-3); Copper Ammoniumcarbonate (CAS 33113-08-5); Copper oleate (CAS 1120-44-1); Mercury (CAS 7487-94-7; 21908-53-2; 7546-30-7); Benthiavalicarb (CAS 413615-35-7); Cadmium chloride (CAS 10108-64-2); Cedar leaf oil (CAS 8007-20-3); Chlorine (CAS 7782-50-5); Cinnamaldehyde (CAS: 104-55-2); Manganous dimethyldithiocarbamate (CAS 15339-36-3); Neem oil (hydrophobic extract) (CAS 8002-65-1); Paraformaldehyde (CAS 30525-89-4); Sodium bicarbonate (CAS 144-55-8); Potassium bicarbonate (CAS 298-14-6); Sodium diacetate (CAS 127-09-3); Sodium propionate (CAS 137-40-6); TCMTB (CAS 21564-17-0); Benalaxyl-M (CAS 98243-83-5); Metrafenone (CAS 220899-03-6); Penthiopyrad (CAS 183675-82-3) and Tolyfluanid (CAS 731-27-1). The compounds of formulae A-1, A-2, A-3, A-4, A-5, A-6, A-7, A-8, A-9, A-10, A-11, A-12, A-13, A-14, A-15, A-18, A-19, A-20, A-21 and A-22 are described in WO-03/015519. The compound of formula A-15A is described in EP-A-1 006 107. The compounds of formulae A-16, A-17, A-23, A-24, A-25 and A-26 are described in WO-04/067528.

*Bacillus pumilus* GB34 and *Bacillus pumilus* strain QST are described at the U.S. Environmental Protection Agency, U.S. EPA PC Code 006493 and U.S. EPA PC Code 006485, respectively (see: http://www.epa.gov/).

The compound of formula F-1 is described in WO 01/87822. Compounds of formula F-2A and the compound of formula F-2 are described in WO 98/46607. The compound of formula F-3 is described in WO 99/042447. The compound of formula F-4 is described in WO 96/19442. The compound of formula F-5 is described in WO 99/14187. The compound of formula F-6 is described in U.S. Pat. No. 5,945,423 and WO 94/26722. The compound of formula F-7 is described in EP-0-936-213. The compound of formula F-8 is described in U.S. Pat. No. 6,020,332, CN-1-167-568, CN-1-155-977 and EP-0-860-438.

Throughout this document the expression "combination" stands for the various combinations of components A) and B), for example in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the components A) and B) is not essential for working the present invention.

The combinations according to the invention may also comprise more than one of the active components B), if, for example, a broadening of the spectrum of phytopathogenic disease control is desired. For instance, it may be advantageous in the agricultural practice to combine two or three components B) with the any of the compounds of formula I, or with any preferred member of the group of compounds of formula I.

A preferred embodiment of the present invention is represented by those combinations which comprise as component A) a compound of the formula I, wherein $R_1$ is difluoromethyl and $R_2$ is hydrogen, and one component B) as described above.

A preferred embodiment of the present invention is represented by those combinations which comprise as component A) a compound of the formula I, wherein $R_1$ is difluoromethyl and $R_2$ is methyl, and one component B) as described above.

A preferred embodiment of the present invention is represented by those combinations which comprise as component A) a compound of the formula I, wherein $R_1$ is trifluoromethyl and $R_2$ is hydrogen, and one component B) as described above.

A preferred embodiment of the present invention is represented by those combinations which comprise as component A) a compound of the formula I, wherein $R_1$ is trifluoromethyl and $R_2$ is methyl, and one component B) as described above.

A preferred embodiment of the present invention is represented by those combinations which comprise as component A) a compound of the formula Ia (trans)

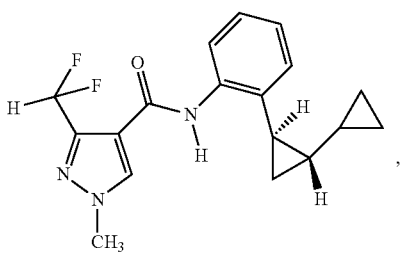
(Ia)

which represents a compound of formula I$_I$, wherein R$_1$ is difluoromethyl and R$_2$ is hydrogen; a compound of formula I$_{II}$, wherein R$_1$ is difluoromethyl and R$_2$ is hydrogen or a mixture in any ratio of a compound of formula I$_I$, wherein R$_1$ is difluoromethyl and R$_2$ is hydrogen, and a compound of formula I$_{II}$, wherein R$_1$ is difluoromethyl and R$_2$ is hydrogen; and one component B) as described above.

Among this embodiment of the invention preference is given to those combinations which comprise as component A) a racemic compound of the formula Ia (trans)

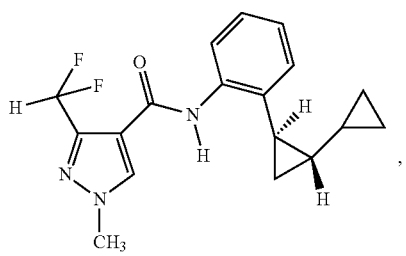
(Ia)

which represents a racemic mixture of a compound of formula I$_I$, wherein R$_1$ is difluoromethyl and R$_2$ is hydrogen, and a compound of formula I$_{II}$, wherein R$_1$ is difluoromethyl and R$_2$ is hydrogen; and one component B) as described above.

A further preferred embodiment of the present invention is represented by those combinations which comprise as component A) a compound of the formula Ib (cis)

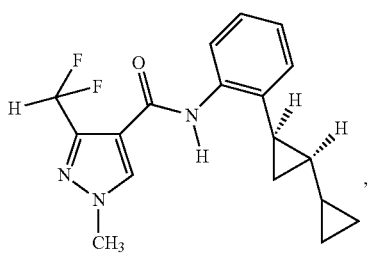
(Ib)

which represents a compound of formula I$_{III}$, wherein R$_1$ is difluoromethyl and R$_2$ is hydrogen; a compound of formula I$_{IV}$, wherein R$_1$ is difluoromethyl and R$_2$ is hydrogen or a mixture in any ratio of a compound of formula I$_{III}$, wherein R$_1$ is difluoromethyl and R$_2$ is hydrogen, and a compound of formula I$_{IV}$, wherein R$_1$ is difluoromethyl and R$_2$ is hydrogen; and one component B) as described above.

A further preferred embodiment of the present invention is represented by those combinations which comprise as component A) a racemic compound of the formula Ib (cis)

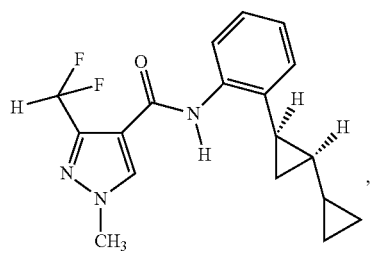
(Ib)

which represents a racemic mixture of a compound of formula I$_{III}$, wherein R$_1$ is difluoromethyl and R$_2$ is hydrogen, and a compound of formula I$_{IV}$, wherein R$_1$ is difluoromethyl and R$_2$ is hydrogen; and one component B) as described above.

A further preferred embodiment of the present invention is represented by those combinations which comprise as component A) a racemic compound of the formula Ic

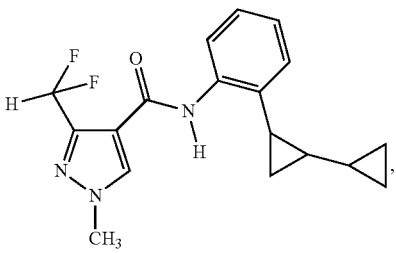
(Ic)

wherein the ratio of racemic compounds of formula Ia, which represent a racemic mixture of compounds of formula I$_I$, wherein R$_1$ is difluoromethyl and R$_2$ is hydrogen, and compounds of formula I$_{II}$, wherein R$_1$ is difluoromethyl and R$_2$ is hydrogen, to racemic compounds of formula Ib, which represent a racemic mixture of compounds of formula I$_{III}$, wherein R$_1$ is difluoromethyl and R$_2$ is hydrogen, and compounds of formula I$_{IV}$, wherein R$_1$ is difluoromethyl and R$_2$ is hydrogen, is from 1:1 to 100:1, and one component B) as described above.

Within said embodiment suitable ratios of racemic compounds of formula Ia, which represent a racemic mixture of compounds of formula I$_I$, wherein R$_1$ is difluoromethyl and R$_2$ is hydrogen, and compounds of formula I$_{II}$, wherein R$_1$ is difluoromethyl and R$_2$ is hydrogen, to racemic compounds of formula Ib, which represent a racemic mixture of compounds of formula I$_{III}$, wherein R$_1$ is difluoromethyl and R$_2$ is hydrogen, and compounds of formula I$_{IV}$, wherein R$_1$ is difluoromethyl and R$_2$ is hydrogen, are ratios such as 1:1, 2:1, 3:1, 4:1, 5:1, 6:1, 7:1, 8:1, 9:1, 10:1, 20:1, 50:1 or 100:1. Preference is given to ratios from 2:1 to 100:1, more preferably 4:1 to 10:1.

A further preferred embodiment of the present invention is represented by those combinations which comprise as component A) a racemic compound of the formula Ic

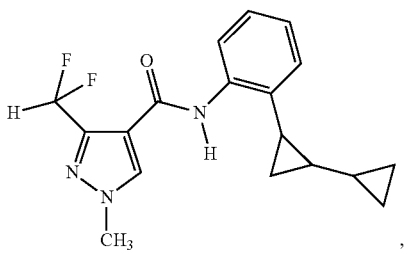

(Ic)

wherein the content of racemic compounds of formula Ia, which represent a racemic mixture of compounds of formula $I_I$, wherein $R_1$ is difluoromethyl and $R_2$ is hydrogen, and compounds of formula $I_{II}$, wherein $R_1$ is difluoromethyl and $R_2$ is hydrogen, is from 65 to 99% by weight, and one component B) as described above.

According to the instant invention, a "racemic mixture" of two enantiomers or a "racemic compound" means a mixture of two enantiomers in a ratio of substantially 50:50 of the two enantiomers.

Preferred components B) are selected from the group consisting of Azoxystrobin; Benalaxyl; Benalaxyl-M; Bitertanol; Boscalid; Carboxin; Carpropamid; Chlorothalonil; Copper; Cyazofamid; Cymoxanil; Cyproconazole; Cyprodinil; Difenoconazole; Famoxadone; Fenamidone; Fenhexamide; Fenpiclonil; Fluazinam; Fludioxonil; Fluquinconazole; Fluoxastrobin; Flutolanil; Flutriafol; Guazatine; Hexaconazole; Hymexazole; Imazalil; Ipconazole; Iprodione; Mancozeb; Metalaxyl; Mefenoxam; Metconazole; Metrafenone; Nuarimol; Oxpoconazole; Paclobutrazol; Pencycuron; Penthiopyrad; Picoxystrobin; Prochloraz; Procymidone; Prothioconazole; Pyraclostrobin; Pyrimethanil; Pyroquilon; Silthiofam; Tebuconazole; Tetraconazole; Thiabendazole; Thiram; Triadimenol; Triazoxide; Trifloxystrobin; Triticonazole; Thiamethoxam; Tefluthrin; Abamectin; Propiconazole; Fenpropimorph; Fenpropidin; a compound of formula F-1

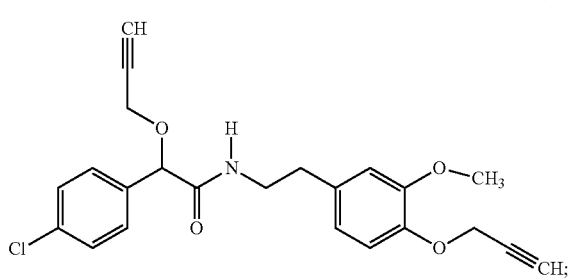

(F-1)

a compound of formula F-2

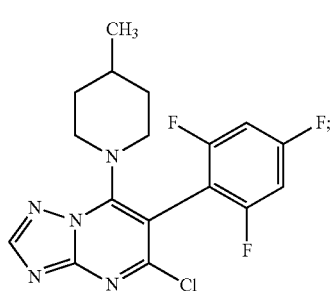

(F-2)

and Epoxiconazole.

More preferred components B) are selected from the group consisting of Azoxystrobin; Picoxystrobin; Cyproconazole; Difenoconazole; Propiconazole; Fludioxonil; Cyprodinil; Fenpropimorph; Fenpropidin; a compound of formula F-1

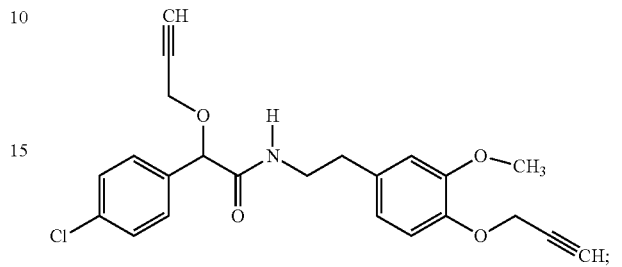

(F-1)

a compound of formula F-2

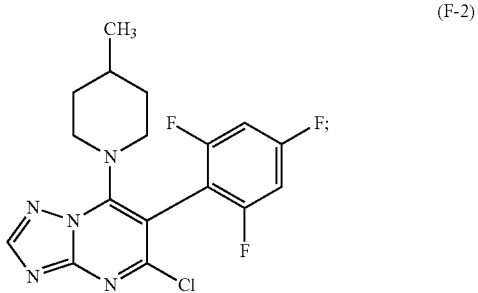 [SMILES: CC1CCN(c2c(-c3c(F)cc(F)cc3F)c(Cl)nc3ncnn23)CC1]

(F-2)

Chlorothalonil; Epoxiconazole; Prothioconazole and Thiabendazole.

More preferred component B) is Azoxystrobin; Fludioxonil; Difenoconazole; Cyproconazole or Thiabendazole.

Most preferred component B) is Azoxystrobin; Fludioxonil or Difenoconazole.

A preferred embodiment of the present invention is represented by those combinations which comprise as component A) a compound of the formula I, wherein $R_1$ is difluoromethyl and $R_2$ is hydrogen, and one component B) selected from the group consisting of Azoxystrobin; Benalaxyl; Benalaxyl-M; Bitertanol; Boscalid; Carboxin; Carpropamid; Chlorothalonil; Copper; Cyazofamid; Cymoxanil; Cyproconazole; Cyprodinil; Difenoconazole; Famoxadone; Fenamidone; Fenhexamide; Fenpiclonil; Fluazinam; Fludioxonil; Fluquinconazole; Fluoxastrobin; Flutolanil; Flutriafol; Guazatine; Hexaconazole; Hymexazole; Imazalil; Ipconazole; Iprodione; Mancozeb; Metalaxyl; Mefenoxam; Metconazole; Metrafenone; Nuarimol; Oxpoconazole; Paclobutrazol; Pencycuron; Penthiopyrad; Picoxystrobin; Prochloraz; Procymidone; Prothioconazole; Pyraclostrobin; Pyrimethanil; Pyroquilon; Silthiofam; Tebuconazole; Tetraconazole; Thiabendazole; Thiram; Triadimenol; Triazoxide; Trifloxystrobin; Triticonazole; Thiamethoxam; Tefluthrin; Abamectin; Propiconazole; Fenpropimorph; Fenpropidin; a compound of formula F-1

(F-1)

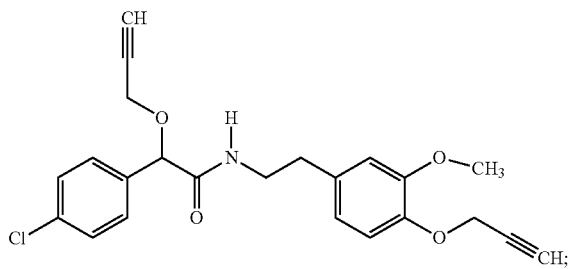

a compound of formula F-2

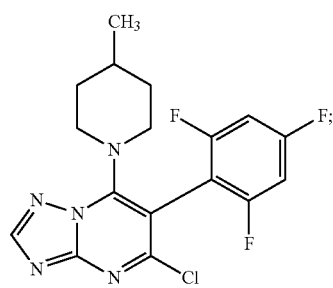

and Epoxiconazole.

A preferred embodiment of the present invention is represented by those combinations which comprise as component A) a compound of the formula I, wherein $R_1$ is difluoromethyl and $R_2$ is methyl, and one component B) selected from the group consisting of Azoxystrobin; Benalaxyl; Benalaxyl-M; Bitertanol; Boscalid; Carboxin; Carpropamid; Chlorothalonil; Copper; Cyazofamid; Cymoxanil; Cyproconazole; Cyprodinil; Difenoconazole; Famoxadone; Fenamidone; Fenhexamide; Fenpiclonil; Fluazinam; Fludioxonil; Fluquinconazole; Fluoxastrobin; Flutolanil; Flutriafol; Guazatine; Hexaconazole; Hymexazole; Imazalil; Ipconazole; Iprodione; Mancozeb; Metalaxyl; Mefenoxam; Metconazole; Metrafenone; Nuarimol; Oxpoconazole; Paclobutrazol; Pencycuron; Penthiopyrad; Picoxystrobin; Prochloraz; Procymidone; Prothioconazole; Pyraclostrobin; Pyrimethanil; Pyroquilon; Silthiofam; Tebuconazole; Tetraconazole; Thiabendazole; Thiram; Triadimenol; Triazoxide; Trifloxystrobin; Triticonazole; Thiamethoxam; Tefluthrin; Abamectin; Propiconazole; Fenpropimorph; Fenpropidin; a compound of formula F-1

(F-1)

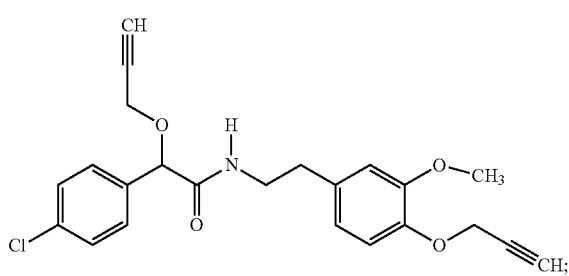

a compound of formula F-2

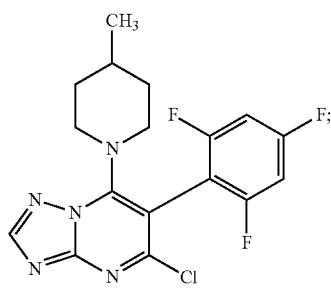

and Epoxiconazole.

A preferred embodiment of the present invention is represented by those combinations which comprise as component A) a compound of the formula I, wherein $R_1$ is trifluoromethyl and $R_2$ is methyl, and one component B) selected from the group consisting of Azoxystrobin; Benalaxyl; Benalaxyl-M; Bitertanol; Boscalid; Carboxin; Carpropamid; Chlorothalonil; Copper; Cyazofamid; Cymoxanil; Cyproconazole; Cyprodinil; Difenoconazole; Famoxadone; Fenamidone; Fenhexamide; Fenpiclonil; Fluazinam; Fludioxonil; Fluquinconazole; Fluoxastrobin; Flutolanil; Flutriafol; Guazatine; Hexaconazole; Hymexazole; Imazalil; Ipconazole; Iprodione; Mancozeb; Metalaxyl; Mefenoxam; Metconazole; Metrafenone; Nuarimol; Oxpoconazole; Paclobutrazol; Pencycuron; Penthiopyrad; Picoxystrobin; Prochloraz; Procymidone; Prothioconazole; Pyraclostrobin; Pyrimethanil; Pyroquilon; Silthiofam; Tebuconazole; Tetraconazole; Thiabendazole; Thiram; Triadimenol; Triazoxide; Trifloxystrobin; Triticonazole; Thiamethoxam; Tefluthrin; Abamectin; Propiconazole; Fenpropimorph; Fenpropidin; a compound of formula F-1

(F-1)

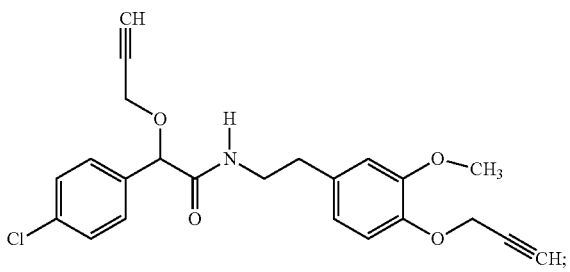

a compound of formula F-2

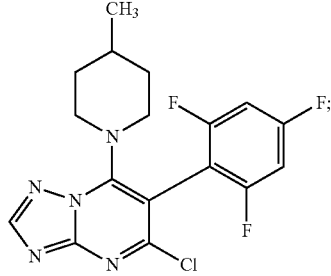

and Epoxiconazole.

A preferred embodiment of the present invention is represented by those combinations which comprise as component A) a compound of the formula Ia (trans)

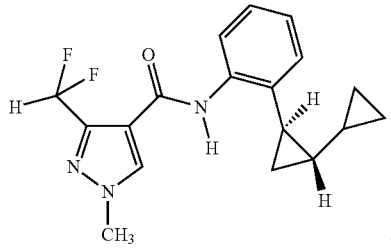

which represents a compound of formula $I_I$, wherein $R_1$ is difluoromethyl and $R_2$ is hydrogen; a compound of formula $I_{II}$, wherein $R_1$ is difluoromethyl and $R_2$ is hydrogen or a mixture in any ratio of a compound of formula $I_I$, wherein $R_1$ is difluoromethyl and $R_2$ is hydrogen, and a compound of formula $I_{II}$, wherein $R_1$ is difluoromethyl and $R_2$ is hydrogen; and one component B) selected from the group consisting of Azoxystrobin; Benalaxyl; Benalaxyl-M; Bitertanol; Boscalid; Carboxin; Carpropamid; Chlorothalonil; Copper; Cyazofamid; Cymoxanil; Cyproconazole; Cyprodinil; Difenoconazole; Famoxadone; Fenamidone; Fenhexamide; Fenpiclonil; Fluazinam; Fludioxonil; Fluquinconazole; Fluoxastrobin; Flutolanil; Flutriafol; Guazatine; Hexaconazole; Hymexazole; Imazalil; Ipconazole; Iprodione; Mancozeb; Metalaxyl; Mefenoxam; Metconazole; Metrafenone; Nuarimol; Oxpoconazole; Paclobutrazol; Pencycuron; Penthiopyrad; Picoxystrobin; Prochloraz; Procymidone; Prothioconazole; Pyraclostrobin; Pyrimethanil; Pyroquilon; Silthiofam; Tebuconazole; Tetraconazole; Thiabendazole; Thiram; Triadimenol; Triazoxide; Trifloxystrobin; Triticonazole; Thiamethoxam; Tefluthrin; Abamectin; Propiconazole; Fenpropimorph; Fenpropidin; a compound of formula F-1

Among this embodiment preference is given to those combinations which comprise as component A) a racemic compound of the formula Ia (trans)

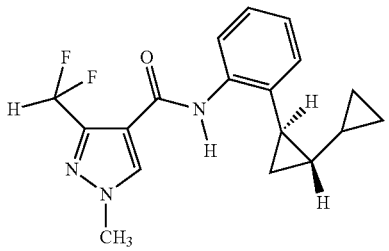

which represents a racemic mixture of a compound of formula $I_I$, wherein $R_1$ is difluoromethyl and $R_2$ is hydrogen, and a compound of formula $I_{II}$, wherein $R_1$ is difluoromethyl and $R_2$ is hydrogen; and one component B) selected from the group consisting of Azoxystrobin; Benalaxyl; Benalaxyl-M; Bitertanol; Boscalid; Carboxin; Carpropamid; Chlorothalonil; Copper; Cyazofamid; Cymoxanil; Cyproconazole; Cyprodinil; Difenoconazole; Famoxadone; Fenamidone; Fenhexamide; Fenpiclonil; Fluazinam; Fludioxonil; Fluquinconazole; Fluoxastrobin; Flutolanil; Flutriafol; Guazatine; Hexaconazole; Hymexazole; Imazalil; Ipconazole; Iprodione; Mancozeb; Metalaxyl; Mefenoxam; Metconazole; Metrafenone; Nuarimol; Oxpoconazole; Paclobutrazol; Pencycuron; Penthiopyrad; Picoxystrobin; Prochloraz; Procymidone; Prothioconazole; Pyraclostrobin; Pyrimethanil; Pyroquilon; Silthiofam; Tebuconazole; Tetraconazole; Thiabendazole; Thiram; Triadimenol; Triazoxide; Trifloxystrobin; Triticonazole; Thiamethoxam; Tefluthrin; Abamectin; Propiconazole; Fenpropimorph; Fenpropidin; a compound of formula F-1

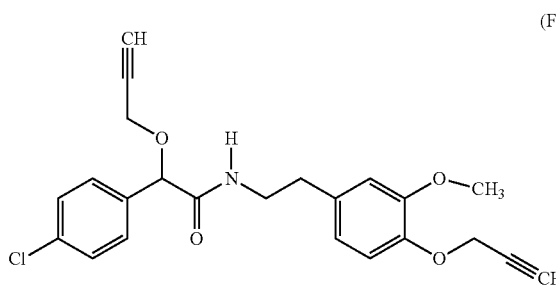

a compound of formula F-2

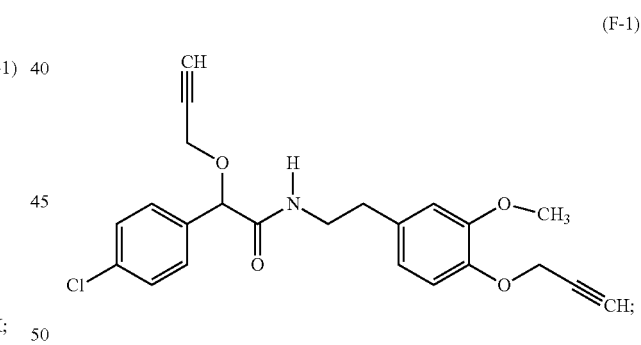

a compound of formula F-2

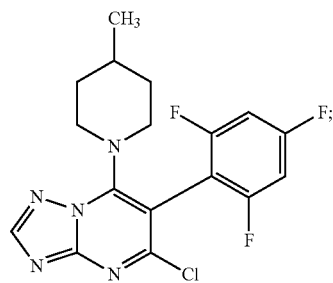

and Epoxiconazole.

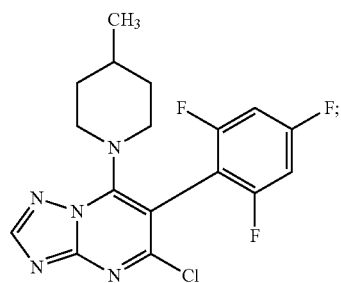

and Epoxiconazole.

A further preferred embodiment of the present invention is represented by those combinations which comprise as component A) a compound of the formula Ib (cis)

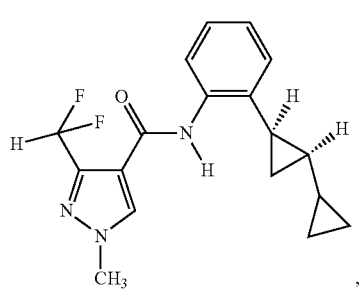
(Ib)

which represents a compound of formula $I_{III}$, wherein $R_1$ is difluoromethyl and $R_2$ is hydrogen; a compound of formula $I_{IV}$, wherein $R_1$ is difluoromethyl and $R_2$ is hydrogen or a mixture in any ratio of a compound of formula $I_{III}$, wherein $R_1$ is difluoromethyl and $R_2$ is hydrogen, and a compound of formula $I_{IV}$, wherein $R_1$ is difluoromethyl and $R_2$ is hydrogen; and one component B) selected from the group consisting of Azoxystrobin; Benalaxyl; Benalaxyl-M; Bitertanol; Boscalid; Carboxin; Carpropamid; Chlorothalonil; Copper; Cyazofamid; Cymoxanil; Cyproconazole; Cyprodinil; Difenoconazole; Famoxadone; Fenamidone; Fenhexamide; Fenpiclonil; Fluazinam; Fludioxonil; Fluquinconazole; Fluoxastrobin; Flutolanil; Flutriafol; Guazatine; Hexaconazole; Hymexazole; Imazalil; Ipconazole; Iprodione; Mancozeb; Metalaxyl; Mefenoxam; Metconazole; Metrafenone; Nuarimol; Oxpoconazole; Paclobutrazol; Pencycuron; Penthiopyrad; Picoxystrobin; Prochloraz; Procymidone; Prothioconazole; Pyraclostrobin; Pyrimethanil; Pyroquilon; Silthiofam; Tebuconazole; Tetraconazole; Thiabendazole; Thiram; Triadimenol; Triazoxide; Trifloxystrobin; Triticonazole; Thiamethoxam; Tefluthrin; Abamectin; Propiconazole; Fenpropimorph; Fenpropidin; a compound of formula F-1

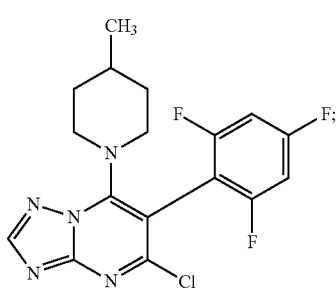
(F-1)

a compound of formula F-2

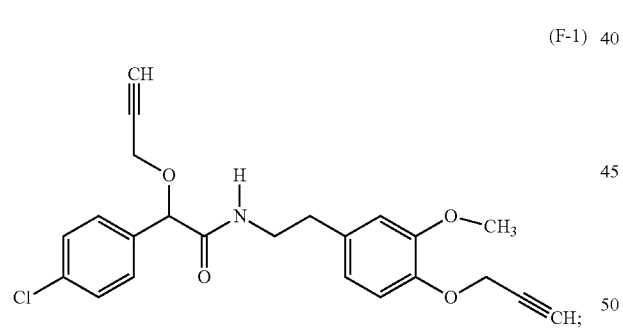
(F-2)

and Epoxiconazole.

A further preferred embodiment of the present invention is represented by those combinations which comprise as component A) a racemic compound of the formula Ib (cis)

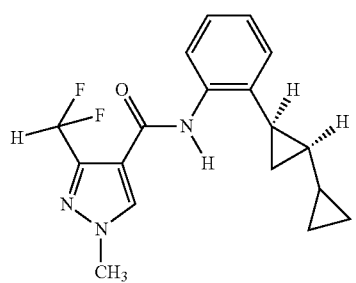
(Ib)

which represents a racemic mixture of a compound of formula $I_{III}$, wherein $R_1$ is difluoromethyl and $R_2$ is hydrogen, and a compound of formula $I_{IV}$, wherein $R_1$ is difluoromethyl and $R_2$ is hydrogen; and one component B) selected from the group consisting of Azoxystrobin; Benalaxyl; Benalaxyl-M; Bitertanol; Boscalid; Carboxin; Carpropamid; Chlorothalonil; Copper; Cyazofamid; Cymoxanil; Cyproconazole; Cyprodinil; Difenoconazole; Famoxadone; Fenamidone; Fenhexamide; Fenpiclonil; Fluazinam; Fludioxonil; Fluquinconazole; Fluoxastrobin; Flutolanil; Flutriafol; Guazatine; Hexaconazole; Hymexazole; Imazalil; Ipconazole; Iprodione; Mancozeb; Metalaxyl; Mefenoxam; Metconazole; Metrafenone; Nuarimol; Oxpoconazole; Paclobutrazol; Pencycuron; Penthiopyrad; Picoxystrobin; Prochloraz; Procymidone; Prothioconazole; Pyraclostrobin; Pyrimethanil; Pyroquilon; Silthiofam; Tebuconazole; Tetraconazole; Thiabendazole; Thiram; Triadimenol; Triazoxide; Trifloxystrobin; Triticonazole; Thiamethoxam; Tefluthrin; Abamectin; Propiconazole; Fenpropimorph; Fenpropidin; a compound of formula F-1

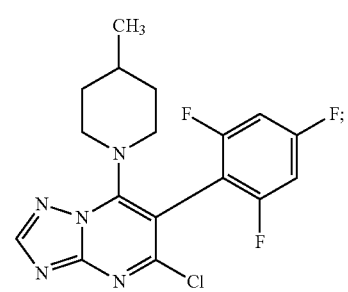
(F-1)

a compound of formula F-2 and Epoxiconazole.

A further preferred embodiment of the present invention is represented by those combinations which comprise as component A) a racemic compound of the formula Ic

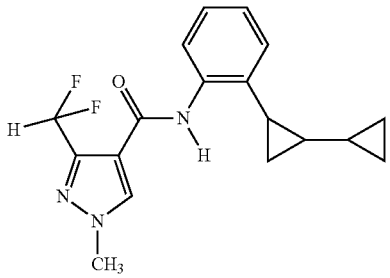

(Ic)

wherein the ratio of compounds of formula Ia, which represent a racemic mixture of compounds of formula I$_I$, wherein R$_1$ is difluoromethyl and R$_2$ is hydrogen, and compounds of formula I$_{II}$, wherein R$_1$ is difluoromethyl and R$_2$ is hydrogen, to compounds of formula Ib, which represent a racemic mixture of compounds of formula I$_{III}$, wherein R$_1$ is difluoromethyl and R$_2$ is hydrogen, and compounds of formula I$_{IV}$, wherein R$_1$ is difluoromethyl and R$_2$ is hydrogen, is from 2:1 to 100:1, and one component B) selected from the group consisting of Azoxystrobin; Benalaxyl; Benalaxyl-M; Bitertanol; Boscalid; Carboxin; Carpropamid; Chlorothalonil; Copper; Cyazofamid; Cymoxanil; Cyproconazole; Cyprodinil; Difenoconazole; Famoxadone; Fenamidone; Fenhexamide; Fenpiclonil; Fluazinam; Fludioxonil; Fluquinconazole; Fluoxastrobin; Flutolanil; Flutriafol; Guazatine; Hexaconazole; Hymexazole; Imazalil; Ipconazole; Iprodione; Mancozeb; Metalaxyl; Mefenoxam; Metconazole; Metrafenone; Nuarimol; Oxpoconazole; Paclobutrazol; Pencycuron; Penthiopyrad; Picoxystrobin; Prochloraz; Procymidone; Prothioconazole; Pyraclostrobin; Pyrimethanil; Pyroquilon; Silthiofam; Tebuconazole; Tetraconazole; Thiabendazole; Thiram; Triadimenol; Triazoxide; Trifloxystrobin; Triticonazole; Thiamethoxam; Tefluthrin; Abamectin; Propiconazole; Fenpropimorph; Fenpropidin; a compound of formula F-1

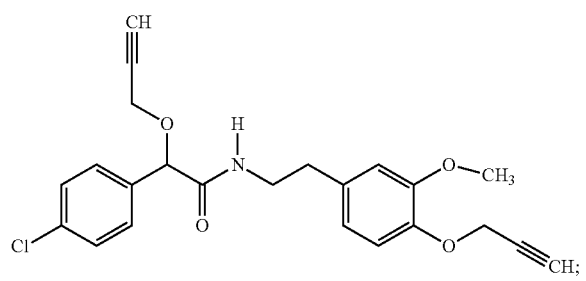

(F-1)

a compound of formula F-2

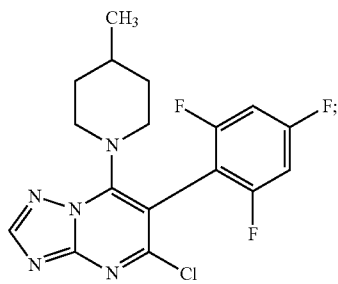

(F-2)

and Epoxiconazole.

A further preferred embodiment of the present invention is represented by those combinations which comprise as component A) a racemic compound of the formula Ic

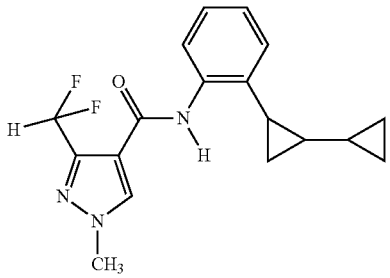

(Ic)

wherein the content of compounds of formula Ia, which represent a racemic mixture of compounds of formula I$_I$, wherein R$_1$ is difluoromethyl and R$_2$ is hydrogen, and compounds of formula I$_{II}$, wherein R$_1$ is difluoromethyl and R$_2$ is hydrogen, is from 65 to 99% by weight, and one component B) selected from the group consisting of Azoxystrobin; Benalaxyl; Benalaxyl-M; Bitertanol; Boscalid; Carboxin; Carpropamid; Chlorothalonil; Copper; Cyazofamid; Cymoxanil; Cyproconazole; Cyprodinil; Difenoconazole; Famoxadone; Fenamidone; Fenhexamide; Fenpiclonil; Fluazinam; Fludioxonil; Fluquinconazole; Fluoxastrobin; Flutolanil; Flutriafol; Guazatine; Hexaconazole; Hymexazole; Imazalil; Ipconazole; Iprodione; Mancozeb; Metalaxyl; Mefenoxam; Metconazole; Metrafenone; Nuarimol; Oxpoconazole; Paclobutrazol; Pencycuron; Penthiopyrad; Picoxystrobin; Prochloraz; Procymidone; Prothioconazole; Pyraclostrobin; Pyrimethanil; Pyroquilon; Silthiofam; Tebuconazole; Tetraconazole; Thiabendazole; Thiram; Triadimenol; Triazoxide; Trifloxystrobin; Triticonazole; Thiamethoxam; Tefluthrin; Abamectin; Propiconazole; Fenpropimorph; Fenpropidin; a compound of formula F-1

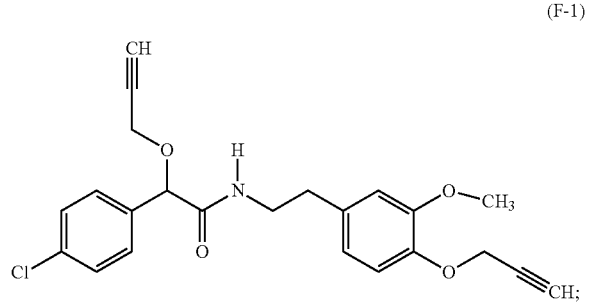 [SMILES: C#CCOc1ccc(CCNC(=O)C(OCC#C)c2ccc(Cl)cc2)cc1OC]
(F-1)

a compound of formula F-2

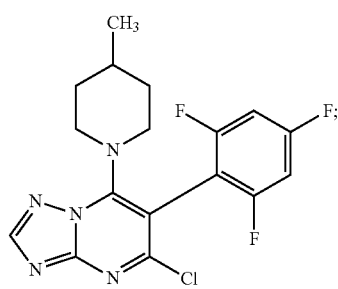
(F-2)

and Epoxiconazole.

A preferred embodiment of the present invention is represented by those combinations which comprise as component A) a compound of the formula I, wherein $R_1$ is difluoromethyl and $R_2$ is hydrogen, and one component B) selected from the group consisting of Azoxystrobin; Fludioxonil; Difenoconazole; Cyproconazole or Thiabendazole.

A preferred embodiment of the present invention is represented by those combinations which comprise as component A) a racemic compound of the formula Ia (trans)

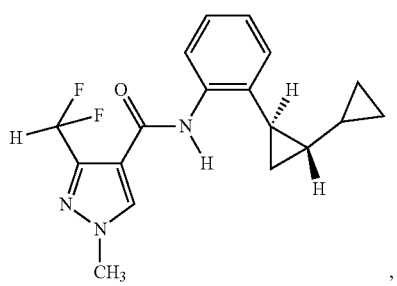
(Ia)

which represents a racemic mixture of a compound of formula $I_I$, wherein $R_1$ is difluoromethyl and $R_2$ is hydrogen, and a compound of formula $I_{II}$, wherein $R_1$ is difluoromethyl and $R_2$ is hydrogen; and one component B) selected from the group consisting of Azoxystrobin; Fludioxonil; Difenoconazole; Cyproconazole or Thiabendazole.

A further preferred embodiment of the present invention is represented by those combinations which comprise as component A) a racemic compound of the formula Ic

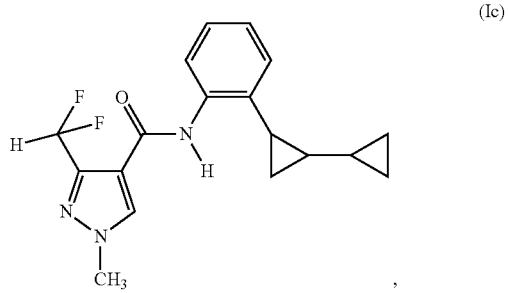 [SMILES: Cn1cc(C(=O)Nc2ccccc2C2CC2C2CC2)c(C(F)F)n1]
(Ic)

wherein the ratio of compounds of formula Ia, which represent a racemic mixture of compounds of formula $I_I$, wherein $R_1$ is difluoromethyl and $R_2$ is hydrogen, and compounds of formula $I_{II}$, wherein $R_1$ is difluoromethyl and $R_2$ is hydrogen, to compounds of formula Ib, which represent a racemic mixture of compounds of formula $I_{III}$, wherein $R_1$ is difluoromethyl and $R_2$ is hydrogen, and compounds of formula $I_{IV}$, wherein $R_1$ is difluoromethyl and $R_2$ is hydrogen, is from 2:1 to 100:1, and one component B) selected from the group consisting of Azoxystrobin; Fludioxonil; Difenoconazole; Cyproconazole or Thiabendazole.

A further preferred embodiment of the present invention is represented by those combinations which comprise as component A) a racemic compound of the formula Ic

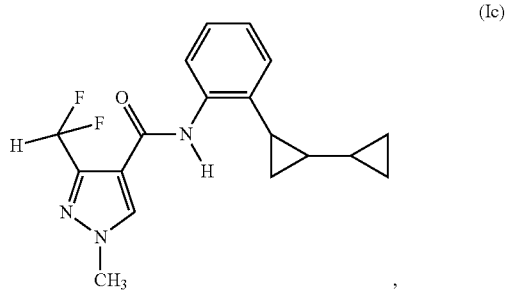 [SMILES: Cn1cc(C(=O)Nc2ccccc2C2CC2C2CC2)c(C(F)F)n1]
(Ic)

wherein the content of compounds of formula Ia, which represent a racemic mixture of compounds of formula $I_I$, wherein $R_1$ is difluoromethyl and $R_2$ is hydrogen, and compounds of formula $I_{II}$, wherein $R_1$ is difluoromethyl and $R_2$ is hydrogen, is from 65 to 99% by weight, and one component B) selected from the group consisting of Azoxystrobin; Fludioxonil; Difenoconazole; Cyproconazole or Thiabendazole.

A preferred embodiment of the present invention is represented by those combinations which comprise as component A) a compound of the formula I, wherein $R_1$ is difluoromethyl and $R_2$ is hydrogen, and one component B) selected from the group consisting of Azoxystrobin; Difenoconazole and Fludioxonil.

A preferred embodiment of the present invention is represented by those combinations which comprise as component A) a racemic compound of the formula Ia (trans)

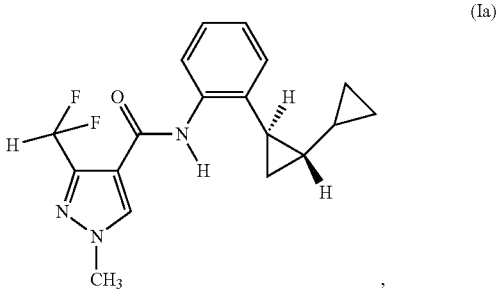 [SMILES: Cn1cc(C(=O)Nc2ccccc2[C@@H]2C[C@H]2C2CC2)c(C(F)F)n1]

(Ia)

which represents a racemic mixture of a compound of formula I$_I$, wherein R$_1$ is difluoromethyl and R$_2$ is hydrogen, and a compound of formula I$_{II}$, wherein R$_1$ is difluoromethyl and R$_2$ is hydrogen; and one component B) selected from the group consisting of Azoxystrobin; Difenoconazole and Fludioxonil.

A further preferred embodiment of the present invention is represented by those combinations which comprise as component A) a racemic compound of the formula Ic

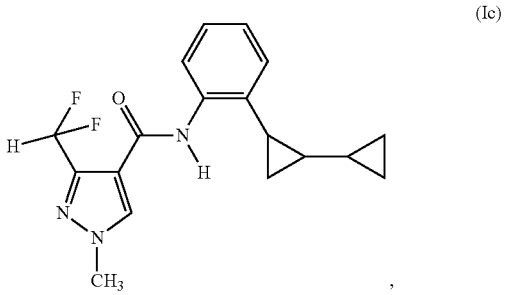 [SMILES: Cn1cc(C(=O)Nc2ccccc2C2CC2C2CC2)c(C(F)F)n1]

(Ic)

wherein the ratio of compounds of formula Ia, which represent a racemic mixture of compounds of formula I$_I$, wherein R$_1$ is difluoromethyl and R$_2$ is hydrogen, and compounds of formula I$_{II}$, wherein R$_1$ is difluoromethyl and R$_2$ is hydrogen, to compounds of formula Ib, which represent a racemic mixture of compounds of formula I$_{III}$, wherein R$_1$ is difluoromethyl and R$_2$ is hydrogen, and compounds of formula I$_{IV}$, wherein R$_1$ is difluoromethyl and R$_2$ is hydrogen, is from 2:1 to 100:1, and one component B) selected from the group consisting of Azoxystrobin; Difenoconazole and Fludioxonil.

A further preferred embodiment of the present invention is represented by those combinations which comprise as component A) a racemic compound of the formula Ic

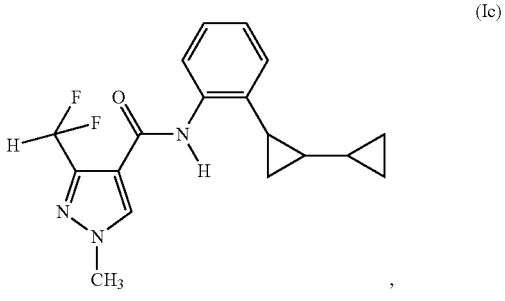 [SMILES: Cn1cc(C(=O)Nc2ccccc2C2CC2C2CC2)c(C(F)F)n1]

(Ic)

wherein the content of compounds of formula Ia, which represent a racemic mixture of compounds of formula I$_I$, wherein R$_1$ is difluoromethyl and R$_2$ is hydrogen, and compounds of formula I$_{II}$, wherein R$_1$ is difluoromethyl and R$_2$ is hydrogen, is from 65 to 99% by weight, and one component B) selected from the group consisting of Azoxystrobin; Difenoconazole and Fludioxonil.

The active ingredient combinations are effective especially against phytopathogenic fungi belonging to the following classes: Ascomycetes (e.g. *Venturia, Podosphaera, Erysiphe, Monilinia, Mycosphaerella, Uncinula*); Basidiomycetes (e.g. the genus *Hemileia, Rhizoctonia, Puccinia, Ustilago, Tilletia*); Fungi imperfecti (also known as *Deuteromycetes*; e.g. *Botrytis, Helminthosporium, Rhynchosporium, Fusarium, Septoria, Cercospora, Alternaria, Pyricularia* and *Pseudocercosporella herpotrichoides*); Oomycetes (e.g. *Phytophthora, Peronospora, Pseudoperonospora, Albugo, Bremia, Pythium, Pseudosclerospora, Plasmopara*).

According to the invention "useful plants" typically comprise the following species of plants: cereals, such as wheat, barley, rye or oats; beet, such as sugar beet or fodder beet; fruits, such as pomes, stone fruits or soft fruits, for example apples, pears, plums, peaches, almonds, cherries, strawberries, raspberries or blackberries; leguminous plants, such as beans, lentils, peas or soybeans; oil plants, such as rape, mustard, poppy, olives, sunflowers, coconut, castor oil plants, cocoa beans or groundnuts; cucumber plants, such as marrows, cucumbers or melons; fibre plants, such as cotton, flax, hemp or jute; citrus fruit, such as oranges, lemons, grapefruit or mandarins; vegetables, such as spinach, lettuce, asparagus, cabbages, carrots, onions, tomatoes, potatoes, cucurbits or paprika; lauraceae, such as avocados, cinnamon or camphor; maize; tobacco; nuts; coffee; sugar cane; tea; vines; hops; durian; bananas; natural rubber plants; turf or ornamentals, such as flowers, shrubs, broad-leaved trees or evergreens, for example conifers. This list does not represent any limitation.

The term "useful plants" is to be understood as including also useful plants that have been rendered tolerant to herbicides like bromoxynil or classes of herbicides (such as, for example, HPPD inhibitors, ALS inhibitors, for example primisulfuron, prosulfuron and trifloxysulfuron, EPSPS (5-enol-pyrovyl-shikimate-3-phosphate-synthase) inhibitors, GS (glutamine synthetase) inhibitors) as a result of conventional methods of breeding or genetic engineering. An example of a crop that has been rendered tolerant to imidazolinones, e.g. imazamox, by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady®, Herculex I® and LibertyLink®.

The term "useful plants" is to be understood as including also useful plants which have been so transformed by the use of recombinant DNA techniques that they are capable of synthesising one or more selectively acting toxins, such as are known, for example, from toxin-producing bacteria, especially those of the genus *Bacillus*.

Toxins that can be expressed by such transgenic plants include, for example, insecticidal proteins, for example insecticidal proteins from *Bacillus cereus* or *Bacillus popliae*; or insecticidal proteins from *Bacillus thuringiensis*, such as δ-endotoxins, e.g. CryIA(b), CryIA(c), CryIF, CryIF (a2), CryIIA(b), CryIIIA, CryIIIB(b1) or Cry9c, or vegetative insecticidal proteins (VIP), e.g. VIP1, VIP2, VIP3 or VIP3A; or insecticidal proteins of bacteria colonising nematodes, for example *Photorhabdus* spp. or *Xenorhabdus* spp., such as *Photorhabdus luminescens, Xenorhabdus nematophilus*; toxins produced by animals, such as scorpion toxins, arachnid toxins, wasp toxins and other insect-specific neurotoxins; toxins produced by fungi, such as *Streptomycetes toxins*, plant lectins, such as pea lectins, barley lectins or snowdrop lectins; agglutinins; proteinase inhibitors, such as trypsine inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyl-transferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

In the context of the present invention there are to be understood by δ-endotoxins, for example CryIA(b), CryIA (c), CryIF, CryIF(a2), CryIIA(b), CryIIIA, CryIIIB(b1) or Cry9c, or vegetative insecticidal proteins (VIP), for example VIP1, VIP2, VIP3 or VIP3A, expressly also hybrid toxins, truncated toxins and modified toxins. Hybrid toxins are produced recombinantly by a new combination of different domains of those proteins (see, for example, WO 02/15701). An example for a truncated toxin is a truncated CryIA(b), which is expressed in the Bt11 maize from Syngenta Seed SAS, as described below. In the case of modified toxins, one or more amino acids of the naturally occurring toxin are replaced. In such amino acid replacements, preferably non-naturally present protease recognition sequences are inserted into the toxin, such as, for example, in the case of CryIIIA055, a cathepsin-D-recognition sequence is inserted into a CryIIIA toxin (see WO 03/018810)

Examples of such toxins or transgenic plants capable of synthesising such toxins are disclosed, for example, in EP-A-0 374 753, WO 93/07278, WO 95/34656, EP-A-0 427 529, EP-A-451 878 and WO 03/052073.

The processes for the preparation of such transgenic plants are generally known to the person skilled in the art and are described, for example, in the publications mentioned above. CryI-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (Coleoptera), two-winged insects (Diptera) and butterflies (Lepidoptera).

Transgenic plants containing one or more genes that code for an insecticidal resistance and express one or more toxins are known and some of them are commercially available. Examples of such plants are: YieldGard® (maize variety that expresses a CryIA(b) toxin); YieldGard Rootworm® (maize variety that expresses a CryIIIB(b1) toxin); YieldGard Plus® (maize variety that expresses a CryIA(b) and a CryIIIB(b1) toxin); Starlink® (maize variety that expresses a Cry9(c) toxin); Herculex I® (maize variety that expresses a CryIF(a2) toxin and the enzyme phosphinothricine N-acetyltransferase (PAT) to achieve tolerance to the herbicide glufosinate ammonium); NuCOTN 33B® (cotton variety that expresses a CryIA(c) toxin); Bollgard I® (cotton variety that expresses a CryIA(c) toxin); Bollgard II® (cotton variety that expresses a CryIA(c) and a CryIIA(b) toxin); VIPCOT® (cotton variety that expresses a VIP toxin); NewLeaf® (potato variety that expresses a CryIIIA toxin); NatureGard® and Protecta®.

Further examples of such transgenic crops are:

1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated CryIA(b) toxin. Bt11 maize also transgenically expresses the enzyme PAT to achieve tolerance to the herbicide glufosinate ammonium.

2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a CryIA(b) toxin. Bt176 maize also transgenically expresses the enzyme PAT to achieve tolerance to the herbicide glufosinate ammonium.

3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified CryIIIA toxin. This toxin is Cry3A055 modified by insertion of a cathepsin-D-protease recognition sequence. The preparation of such transgenic maize plants is described in WO 03/018810.

4. MON 863 Maize from Monsanto Europe S.A. 270-272 Avenue de Tervuren, B-1150 Brussels, Belgium, registration number C/DE/02/9. MON 863 expresses a CryIIIB(b1) toxin and has resistance to certain Coleoptera insects.

5. IPC 531 Cotton from Monsanto Europe S.A. 270-272 Avenue de Tervuren, B-1150 Brussels, Belgium, registration number C/ES/96/02.

6. 1507 Maize from Pioneer Overseas Corporation, Avenue Tedesco, 7 B-1160 Brussels, Belgium, registration number C/NL/00/10. Genetically modified maize for the expression of the protein CryIF for achieving resistance to certain Lepidoptera insects and of the PAT protein for achieving tolerance to the herbicide glufosinate ammonium.

7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603× MON 810 Maize transgenically expresses the protein CP4 EPSPS, obtained from *Agrobacterium* sp. strain CP4, which imparts tolerance to the herbicide Roundup® (contains glyphosate), and also a CryIA(b) toxin obtained from *Bacillus thuringiensis* subsp. *kurstaki* which brings about tolerance to certain Lepidoptera, include the European corn borer. Transgenic crops of insect-resistant plants are also described in BATS (Zentrum für Biosicherheit and Nachhaltigkeit, Zentrum BATS, Clarastrasse 13, 4058 Basel, Switzerland) Report 2003, (http://bats.ch).

The term "useful plants" is to be understood as including also useful plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818, and EP-A-0 353 191. The methods of producing such transgenic plants are generally known to the person skilled in the art and are described, for example, in the publications mentioned above.

Antipathogenic substances which can be expressed by such transgenic plants include, for example, ion channel blockers, such as blockers for sodium and calcium channels, for example the viral KP1, KP4 or KP6 toxins; stilbene synthases; bibenzyl synthases; chitinases; glucanases; the so-called "pathogenesis-related proteins" (PRPs; see e.g. EP-A-0 392 225); antipathogenic substances produced by microorganisms, for example peptide antibiotics or heterocyclic antibiotics (see e.g. WO 95/33818) or protein or polypeptide factors involved in plant pathogen defence (so-called "plant disease resistance genes", as described in WO 03/000906).

Useful plants of elevated interest in connection with present invention are cereals; maize; turf; vines and vegetables, such as tomatoes, potatoes, cucurbits and lettuce.

The term "locus" of a useful plant as used herein is intended to embrace the place on which the useful plants are growing, where the plant propagation materials of the useful plants are sown or where the plant propagation materials of the useful plants will be placed into the soil. An example for such a locus is a field, on which crop plants are growing.

The term "plant propagation material" is understood to denote generative parts of the plant, such as seeds, which can be used for the multiplication of the latter, and vegetative material, such as cuttings or tubers, for example potatoes. There may be mentioned for example seeds (in the strict sense), roots, fruits, tubers, bulbs, rhizomes and parts of plants. Germinated plants and young plants which are to be transplanted after germination or after emergence from the soil, may also be mentioned. These young plants may be protected before transplantation by a total or partial treatment by immersion. Preferably "plant propagation material" is understood to denote seeds.

The combinations of the present invention may also be used in the field of protecting storage goods against attack of fungi. According to the instant invention, the term "storage goods" is understood to denote natural substances of vegetable and/or animal origin and their processed forms, which have been taken from the natural life cycle and for which long-term protection is desired. Storage goods of vegetable origin, such as plants or parts thereof, for example stalks, leafs, tubers, seeds, fruits or grains, can be protected in the freshly harvested state or in processed form, such as pre-dried, moistened, comminuted, ground, pressed or roasted. Also falling under the definition of storage goods is timber, whether in the form of crude timber, such as construction timber, electricity pylons and barriers, or in the form of finished articles, such as furniture or objects made from wood. Storage goods of animal origin are hides, leather, furs, hairs and the like. The combinations according the present invention can prevent disadvantageous effects such as decay, discoloration or mold. Preferably "storage goods" is understood to denote natural substances of vegetable origin and their processed forms, more preferably fruits and their processed forms, such as pomes, stone fruits, soft fruits and citrus fruits and their processed forms.

In another preferred embodiment of the invention "storage goods" is understood to denote wood.

Therefore a further aspect of the instant invention is a method of protecting natural substances of vegetable and/or animal origin and/or their processed forms, which have been taken from the natural life cycle, which comprises applying to said natural substances of vegetable and/or animal origin or their processed forms a combination of components A) and B) in a synergistically effective amount.

A preferred embodiment is a method of protecting natural substances of vegetable origin and/or their processed forms, which have been taken from the natural life cycle, which comprises applying to said natural substances of vegetable origin or their processed forms a combination of components A) and B) in a synergistically effective amount.

A further preferred embodiment is a method of protecting fruits, preferably pomes, stone fruits, soft fruits and citrus fruits, and/or their processed forms, which have been taken from the natural life cycle, which comprises applying to said natural substances of vegetable origin or their processed forms a combination of components A) and B) in a synergistically effective amount.

The combinations of the present invention may also be used in the field of protecting technical material against attack of fungi. According to the instant invention, the term "technical material" includes paper; carpets; constructions; cooling and heating systems; wall-boards; ventilation and air conditioning systems and the like. The combinations according the present invention can prevent disadvantageous effects such as decay, discoloration or mold. Preferably "storage goods" is understood to denote wall-boards.

The combinations according to the present invention are particularly effective against seedborne and soilborne diseases, such as *Alternaria* spp., *Ascochyta* spp., *Aspergillus* spp., *Penicillium* spp., *Botrytis cinerea*, *Cercospora* spp., *Claviceps purpurea*, *Cochliobolus sativus*, *Colletotrichum* spp., *Diplodia maydis*, *Epicoccum* spp., *Fusarium culmorum*, *Fusarium graminearum*, *Fusarium moniliforme*, *Fusarium oxysporum*, *Fusarium proliferatum*, *Fusarium solani*, *Fusarium subglutinans*, *Gäumannomyces graminis*, *Helminthosporium* spp., *Microdochium nivale*, *Phoma* spp., *Pyrenophora graminea*, *Pyricularia oryzae*, *Rhizoctonia solani*, *Rhizoctonia cerealis*, *Sclerotinia* spp., *Septoria* spp., *Sphacelotheca reilliana*, *Tilletia* spp., *Typhula incarnata*, *Urocystis occulta*, *Ustilago* spp. or *Verticillium* spp.; in particular against pathogens of cereals, such as wheat, barley, rye or oats; maize; rice; cotton; soybean; turf; sugarbeet; oil seed rape; potatoes; pulse crops, such as peas, lentils or chickpea; and sunflower. The combinations according to the present invention are furthermore particularly effective against rusts; powdery mildews; leafspot species; early blights; molds and post harvest dieseases; especially against *Puccinia* in cereals; *Phakopsora* in soybeans; *Hemileia* in coffee; *Phragmidium* in roses; *Alternaria* in potatoes, tomatoes and cucurbits; *Sclerotinia* in vegetables, sunflower and oil seed rape; black rot, red fire, powdery mildew, grey mold and dead arm disease in vine; *Botrytis cinerea* in fruits; *Monilinia* spp. in fruits and *Penicillium* spp. in fruits.

The amount of a combination of the invention to be applied, will depend on various factors, such as the compound employed; the subject of the treatment, such as, for example plants, soil or seeds; the type of treatment, such as, for example spraying, dusting or seed dressing; the purpose of the treatment, such as, for example prophylactic or therapeutic; the type of fungi to be controlled or the application time.

It has been found that the use of components B) in combination with the compound of formula I surprisingly and substantially enhance the effectiveness of the latter against fungi, and vice versa. Additionally, the method of the invention is effective against a wider spectrum of such fungi that can be combated with the active ingredients of this method, when used solely.

The weight ratio of A):B) is so selected as to give a synergistic activity. In general the weight ratio of A):B) is between 2000:1 and 1:1000, preferably between 100:1 and 1:100.

The synergistic activity of the combination is apparent from the fact that the fungicidal activity of the composition of A)+B) is greater than the sum of the fungicidal activities of A) and B).

The method of the invention comprises applying to the useful plants, the locus thereof or propagation material thereof in admixture or separately, a synergistically effective aggregate amount of a compound of formula I and a compound of component B).

Some of said combinations according to the invention have a systemic action and can be used as foliar, soil and seed treatment fungicides.

The combinations of the present invention are of particular interest for controlling a large number of fungi in various useful plants or their seeds, especially in field crops such as potatoes, tobacco and sugarbeets, and wheat, rye, barley, oats, rice, maize, lawns, cotton, soybeans, oil seed rape, pulse crops, sunflower, coffee, sugarcane, fruit and ornamentals in horticulture and viticulture, in vegetables such as cucumbers, beans and cucurbits.

The combinations according to the invention are applied by treating the fungi, the useful plants, the locus thereof, the propagation material thereof, storage goods or technical materials threatened by fungus attack with a synergistically effective aggregate amount of a compound of formula I and a compound of component B).

The combinations according to the invention may be applied before or after infection of the useful plants, the propagation material thereof, storage goods or technical materials by the fungi.

The combinations according to the invention are particularly useful for controlling the following plant diseases:

*Alternaria* species in fruit and vegetables,
*Ascochyta* species in pulse crops,
*Botrytis cinerea* (gray mold) in strawberries, tomatoes, sunflower and grapes,
*Cercospora arachidicola* in groundnuts,
*Cochliobolus sativus* in cereals,
*Colletotrichum* species in pulse crops,
*Erysiphe cichoracearum* and *Sphaerotheca fuliginea* in cucurbits,
*Fusarium graminearum* in cereals and maize,
*Gäumannomyces graminis* in cereals and lawns,
*Helminthosporium maydis* in maize,
*Helminthosporium oryzae* in rice,
*Helminthosporium solani* on potatoes,
*Hemileia vastatrix* on coffee,
*Microdochium nivale* in wheat and rye,
*Phakopsora pachyrhizi* in soybean,
*Puccinia* species in cereals,
*Phragmidium mucronatum* in roses,
*Pyrenophora graminea* in barley,
*Pyricularia oryzae* in rice,
*Rhizoctonia* species in cotton, soybean, cereals, maize, potatoes, rice and lawns,
*Sclerotinia homeocarpa* in lawns,
*Sphacelotheca reilliana* in maize,
*Tilletia* species in cereals,
*Typhula incarnata* in barley,
*Uncinula necator*, *Guignardia bidwellii* and *Phomopsis viticola* in vines,
*Urocystis occulta* in rye,
*Ustilago* species in cereals and maize,
*Monilinia fructicola* on stone fruits,
*Monilinia fructigena* on fruits,
*Monilinia laxa* on stone fruits,
*Penicillium digitatum* on citrus,
*Penicillium expansum* on apples, and
*Penicillium italicum* on citrus, The combinations according to the invention are preventively and/or curatively valuable active ingredients in the field of pest control, even at low rates of application, which have a very favorable biocidal spectrum and are well tolerated by warm-blooded species, fish and plants. The active ingredients according to the invention which are partially known for their insecticidal action act against all or individual developmental stages of normally sensitive, but also resistant, animal pests, such as insects or representatives of the order Acarina. The insecticidal or acaricidal activity of the combinations according to the invention can manifest itself directly, i.e. in destruction of the pests, which takes place either immediately or only after some time has elapsed, for example during ecdysis, or indirectly, for example in a reduced oviposition and/or hatching rate, a good activity corresponding to a destruction rate (mortality) of at least 50 to 60%.

Examples of the abovementioned animal pests are:

from the order Acarina, for example,

*Acarus siro*, *Aceria sheldoni*, *Aculus schlechtendali*, *Amblyomma* spp., *Argas* spp., *Boophilus* spp., *Brevipalpus* spp., *Bryobia praetiosa*, *Calipitrimerus* spp., *Chorioptes* spp., *Dermanyssus gallinae*, *Eotetranychus carpini*, *Eriophyes* spp., *Hyalomma* spp., *Ixodes* spp., *Olygonychus pratensis*, *Ornithodoros* spp., *Panonychus* spp., *Phyllocoptruta oleivora*, *Polyphagotarsonemus latus*, *Psoroptes* spp., *Rhipicephalus* spp., *Rhizoglyphus* spp., *Sarcoptes* spp., *Tarsonemus* spp. and *Tetranychus* spp.;

from the order Anoplura, for example,

*Haematopinus* spp., *Linognathus* spp., *Pediculus* spp., *Pemphigus* spp. and *Phylloxera* spp.;

from the order Coleoptera, for example,

*Agriotes* spp., *Anthonomus* spp., *Atomaria linearis*, *Chaetocnema tibialis*, *Cosmopolites* spp., *Curculio* spp., *Dermestes* spp., *Diabrotica* spp., *Epilachna* spp., *Eremnus* spp., *Leptinotarsa decemlineata*, *Lissorhoptrus* spp., *Melolontha* spp., *Orycaephilus* spp., *Otiorhynchus* spp., *Phlyctinus* spp., *Popillia* spp., *Psylliodes* spp., *Rhizopertha* spp., *Scarabeidae*, *Sitophilus* spp., *Sitotroga* spp., *Tenebrio* spp., *Tribolium* spp. and *Trogoderma* spp.;

from the order Diptera, for example,

*Aedes* spp., *Antherigona soccata*, *Bibio hortulanus*, *Calliphora erythrocephala*, *Ceratitis* spp., *Chrysomyia* spp., *Culex* spp., *Cuterebra* spp., *Dacus* spp., *Drosophila melanogaster*, *Fannia* spp., *Gastrophilus* spp., *Glossina* spp., *Hypoderma* spp., *Hyppobosca* spp., *Liriomyza* spp., *Lucilia* spp., *Melanagromyza* spp., *Musca* spp., *Oestrus* spp., *Orseolia* spp., *Oscinella frit*, *Pegomyia hyoscyami*, *Phorbia* spp., *Rhagoletis pomonella*, *Sciara* spp., *Stomoxys* spp., *Tabanus* spp., *Tannia* spp. and *Tipula* spp.;

from the order Heteroptera, for example,

*Cimex* spp., *Distantiella theobroma*, *Dysdercus* spp., *Euchistus* spp., *Eurygaster* spp., *Leptocorisa* spp., *Nezara* spp., *Piesma* spp., *Rhodnius* spp., *Sahlbergella singularis*, *Scotinophara* spp. and *Triatoma* spp.;

from the order Homoptera, for example,

*Aleurothrixus floccosus*, *Aleyrodes brassicae*, *Aonidiella* spp., *Aphididae*, *Aphis* spp., *Aspidiotus* spp., *Bemisia tabaci*, *Ceroplaster* spp., *Chrysomphalus aonidium*, *Chrysomphalus dictyospermi*, *Coccus hesperidum*, *Empoasca* spp., *Eriosoma larigerum*, *Erythroneura* spp., *Gascardia* spp.,

*Laodelphax* spp., *Lecanium corni*, *Lepidosaphes* spp., *Macrosiphus* spp., *Myzus* spp., *Nephotettix* spp., *Nilaparvata* spp., *Parlatoria* spp., *Pemphigus* spp., *Planococcus* spp., *Pseudaulacaspis* spp., *Pseudococcus* spp., *Psylla* spp., *Pulvinaria aethiopica*, *Quadraspidiotus* spp., *Rhopalosiphum* spp., *Saissetia* spp., *Scaphoideus* spp., *Schizaphis* spp., *Sitobion* spp., *Trialeurodes vaporariorum*, *Trioza erytreae* and *Unaspis citri*;

from the order Hymenoptera, for example,

*Acromyrmex*, *Atta* spp., *Cephus* spp., *Diprion* spp., *Diprionidae*, *Gilpinia polytoma*, *Hoplocampa* spp., *Lasius* spp., *Monomorium pharaonis*, *Neodiprion* spp., *Solenopsis* spp. and *Vespa* spp.;

from the order Isoptera, for example,

*Reticulitermes* spp.;

from the order Lepidoptera, for example,

*Acleris* spp., *Adoxophyes* spp., *Aegeria* spp., *Agrotis* spp., *Alabama argillaceae*, *Amylois* spp., *Anticarsia gemmatalis*, *Archips* spp., *Argyrotaenia* spp., *Autographa* spp., *Busseola fusca*, *Cadra cautella*, *Carposina nipponensis*, *Chilo* spp., *Choristoneura* spp., *Clysia ambiguella*, *Cnaphalocrocis* spp., *Cnephasia* spp., *Cochylis* spp., *Coleophora* spp., *Crocidolomia binotalis*, *Cryptophlebia leucotreta*, *Cydia* spp., *Diatraea* spp., *Diparopsis castanea*, *Earias* spp., *Ephestia* spp., *Eucosma* spp., *Eupoecilia ambiguella*, *Euproctis* spp., *Euxoa* spp., *Grapholita* spp., *Hedya nubiferana*, *Heliothis* spp., *Hellula undalis*, *Hyphantria cunea*, *Keiferia lycopersicella*, *Leucoptera scitella*, *Lithocollethis* spp., *Lobesia botrana*, *Lymantria* spp., *Lyonetia* spp., *Malacosoma* spp., *Mamestra brassicae*, *Manduca sexta*, *Operophtera* spp., *Ostrinia nubilalis*, *Pammene* spp., *Pandemis* spp., *Panolis flammea*, *Pectinophora gossypiela*, *Phthorimaea operculella*, *Pieris rapae*, *Pieris* spp., *Plutella xylostella*, *Prays* spp., *Scirpophaga* spp., *Sesamia* spp., *Sparganothis* spp., *Spodoptera* spp., *Synanthedon* spp., *Thaumetopoea* spp., *Tortrix* spp., *Trichoplusia ni* and *Yponomeuta* spp.;

from the order Mallophaga, for example,

*Damalinea* spp. and *Trichodectes* spp.;

from the order Orthoptera, for example,

*Blatta* spp., *Blattella* spp., *Gryllotalpa* spp., *Leucophaea maderae*, *Locusta* spp., *Periplaneta* spp. and *Schistocerca* spp.;

from the order Psocoptera, for example,

*Liposcelis* spp.;

from the order Siphonaptera, for example,

*Ceratophyllus* spp., *Ctenocephalides* spp. and *Xenopsylla cheopis*;

from the order Thysanoptera, for example,

*Frankliniella* spp., *Hercinothrips* spp., *Scirtothrips aurantii*, *Taeniothrips* spp., *Thrips palmi* and *Thrips tabaci*;

from the order Thysanura, for example,

*Lepisma saccharina*;

nematodes, for example root knot nematodes, stem eelworms and foliar nematodes;

especially *Heterodera* spp., for example *Heterodera schachtii*, *Heterodora avenae* and *Heterodora trifolii*; *Globodera* spp., for example *Globodera rostochiensis*; *Meloidogyne* spp., for example *Meloidogyne incoginita* and *Meloidogyne javanica*; *Radopholus* spp., for example *Radopholus similis*; *Pratylenchus*, for example *Pratylenchus neglectans* and *Pratylenchus penetrans*; *Tylenchulus*, for example *Tylenchulus semipenetrans*; *Longidorus*, *Trichodorus*, *Xiphinema*, *Ditylenchus*, *Aphelenchoides* and *Anguina*;

crucifer flea beetles (*Phyllotreta* spp.);

root maggots (*Delia* spp.) and cabbage seedpod weevil (*Ceutorhynchus* spp.).

The combinations according to the invention can be used for controlling, i. e. containing or destroying, animal pests of the abovementioned type which occur on useful plants in agriculture, in horticulture and in forests, or on organs of useful plants, such as fruits, flowers, foliage, stalks, tubers or roots, and in some cases even on organs of useful plants which are formed at a later point in time remain protected against these animal pests.

When applied to the useful plants the compound of formula I is applied at a rate of 5 to 2000 g a.i./ha, particularly 10 to 1000 g a.i./ha, e.g. 50, 75, 100 or 200 g a.i./ha, in association with 1 to 5000 g a.i./ha, particularly 2 to 2000 g a.i./ha, e.g. 100, 250, 500, 800, 1000, 1500 g a.i./ha of a compound of component B), depending on the class of chemical employed as component B).

In agricultural practice the application rates of the combination according to the invention depend on the type of effect desired, and typically range from 20 to 4000 g of total combination per hectare.

When the combinations of the present invention are used for treating seed, rates of 0.001 to 50 g of a compound of formula I per kg of seed, preferably from 0.01 to 10 g per kg of seed, and 0.001 to 50 g of a compound of component B), per kg of seed, preferably from 0.01 to 10 g per kg of seed, are generally sufficient.

The invention also provides fungicidal compositions comprising a compound of formula I and a compound of component B) in a synergistically effective amount.

The composition of the invention may be employed in any conventional form, for example in the form of a twin pack, a powder for dry seed treatment (DS), an emulsion for seed treatment (ES), a flowable concentrate for seed treatment (FS), a solution for seed treatment (LS), a water dispersible powder for seed treatment (WS), a capsule suspension for seed treatment (CF), a gel for seed treatment (GF), an emulsion concentrate (EC), a suspension concentrate (SC), a suspo-emulsion (SE), a capsule suspension (CS), a water dispersible granule (WG), an emulsifiable granule (EG), an emulsion, water in oil (EO), an emulsion, oil in water (EW), a micro-emulsion (ME), an oil dispersion (OD), an oil miscible flowable (OF), an oil miscible liquid (OL), a soluble concentrate (SL), an ultra-low volume suspension (SU), an ultra-low volume liquid (UL), a technical concentrate (TK), a dispersible concentrate (DC), a wettable powder (WP) or any technically feasible formulation in combination with agriculturally acceptable adjuvants.

Such compositions may be produced in conventional manner, e.g. by mixing the active ingredients with appropriate formulation inerts (diluents, solvents, fillers and optionally other formulating ingredients such as surfactants, biocides, anti-freeze, stickers, thickeners and compounds that provide adjuvancy effects). Also conventional slow release formulations may be employed where long lasting efficacy is intended. Particularly formulations to be applied in spraying forms, such as water dispersible concentrates (e.g. EC, SC, DC, OD, SE, EW, EO and the like), wettable powders and granules, may contain surfactants such as wetting and dispersing agents and other compounds that provide adjuvancy effects, e.g. the condensation product of formaldehyde with naphthalene sulphonate, an alkylarylsulphonate, a lignin sulphonate, a fatty alkyl sulphate, and ethoxylated alkylphenol and an ethoxylated fatty alcohol.

A seed dressing formulation is applied in a manner known per se to the seeds employing the combination of the invention and a diluent in suitable seed dressing formulation form, e.g. as an aqueous suspension or in a dry powder form having good adherence to the seeds. Such seed dressing formulations are known in the art. Seed dressing formulations may contain the single active ingredients or the combination of active ingredients in encapsulated form, e.g. as slow release capsules or microcapsules.

In general, the formulations include from 0.01 to 90% by weight of active agent, from 0 to 20% agriculturally acceptable surfactant and 10 to 99.99% solid or liquid formulation inerts and adjuvant(s), the active agent consisting of at least the compound of formula I together with a compound of component B), and optionally other active agents, particularly microbiocides or conservatives or the like. Concentrated forms of compositions generally contain in between about 2 and 80%, preferably between about 5 and 70% by weight of active agent. Application forms of formulation may for example contain from 0.01 to 20% by weight, preferably from 0.01 to 5% by weight of active agent. Whereas commercial products will preferably be formulated as concentrates, the end user will normally employ diluted formulations.

The Examples which follow serve to illustrate the invention, "active ingredient" denoting a mixture of compound I and a compound of component B) in a specific mixing ratio.

FORMULATION EXAMPLES

| Wettable powders | a) | b) | c) |
|---|---|---|---|
| active ingredient [I:comp B) = 1:3(a), 1:2(b), 1:1(c)] | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| phenol polyethylene glycol ether (7-8 mol of ethylene oxide) | — | 2% | — |
| highly dispersed silicic acid | 5% | 10% | 10% |
| Kaolin | 62% | 27% | — |

The active ingredient is thoroughly mixed with the adjuvants and the mixture is thoroughly ground in a suitable mill, affording wettable powders that can be diluted with water to give suspensions of the desired concentration.

| Powders for dry seed treatment | a) | b) | c) |
|---|---|---|---|
| active ingredient [I:comp B) = 1:3(a), 1:2(b), 1:1(c)] | 25% | 50% | 75% |
| light mineral oil | 5% | 5% | 5% |
| highly dispersed silicic acid | 5% | 5% | — |
| Kaolin | 65% | 40% | — |
| Talcum | — | — | 20 |

The active ingredient is thoroughly mixed with the adjuvants and the mixture is thoroughly ground in a suitable mill, affording powders that can be used directly for seed treatment.

| Emulsifiable concentrate | |
|---|---|
| active ingredient (I:comp B) = 1:6) | 10% |
| octylphenol polyethylene glycol ether (4-5 mol of ethylene oxide) | 3% |
| calcium dodecylbenzenesulfonate | 3% |
| castor oil polyglycol ether (35 mol of ethylene oxide) | 4% |
| Cyclohexanone | 30% |
| xylene mixture | 50% |

Emulsions of any required dilution, which can be used in plant protection, can be obtained from this concentrate by dilution with water.

| Dusts | a) | b) | c) |
|---|---|---|---|
| Active ingredient [I:comp B) = 1:6(a), 1:2(b), 1:10(c)] | 5% | 6% | 4% |
| talcum | 95% | — | — |
| Kaolin | — | 94% | — |
| mineral filler | — | — | 96% |

Ready-for-use dusts are obtained by mixing the active ingredient with the carrier and grinding the mixture in a suitable mill. Such powders can also be used for dry dressings for seed.

| Extruder granules | |
|---|---|
| Active ingredient (I:comp B) = 2:1) | 15% |
| sodium lignosulfonate | 2% |
| carboxymethylcellulose | 1% |
| Kaolin | 82% |

The active ingredient is mixed and ground with the adjuvants, and the mixture is moistened with water. The mixture is extruded and then dried in a stream of air.

| Coated granules | |
|---|---|
| Active ingredient (I:comp B) = 1:10) | 8% |
| polyethylene glycol (mol. wt. 200) | 3% |
| Kaolin | 89% |

The finely ground active ingredient is uniformly applied, in a mixer, to the kaolin moistened with polyethylene glycol. Non-dusty coated granules are obtained in this manner.

| Suspension concentrate | |
|---|---|
| active ingredient (I:comp B) = 1:8) | 40% |
| propylene glycol | 10% |
| nonylphenol polyethylene glycol ether (15 mol of ethylene oxide) | 6% |
| Sodium lignosulfonate | 10% |
| carboxymethylcellulose | 1% |
| silicone oil (in the form of a 75% emulsion in water) | 1% |
| Water | 32% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

| Flowable concentrate for seed treatment | |
|---|---|
| active ingredient (I:comp B) = 1:8) | 40% |
| propylene glycol | 5% |
| copolymer butanol PO/EO | 2% |
| tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Slow Release Capsule Suspension 28 parts of a combination of the compound of formula I and a compound of component B), or of each of these compounds separately, are mixed with 2 parts of an aromatic solvent and 7 parts of toluene diisocyanate/polymethylene-polyphenylisocyanate-mixture (8:1). This mixture is emulsified in a mixture of 1.2 parts of polyvinylalcohol, 0.05 parts of a defoamer and 51.6 parts of water until the desired particle size is achieved. To this emulsion a mixture of 2.8 parts 1,6-diaminohexane in 5.3 parts of water is added. The mixture is agitated until the polymerization reaction is completed.

The obtained capsule suspension is stabilized by adding 0.25 parts of a thickener and 3 parts of a dispersing agent. The capsule suspension formulation contains 28% of the active ingredients. The medium capsule diameter is 8-15 microns.

The resulting formulation is applied to seeds as an aqueous suspension in an apparatus suitable for that purpose.

BIOLOGICAL EXAMPLES

A synergistic effect exists whenever the action of an active ingredient combination is greater than the sum of the actions of the individual components.

The action to be expected E for a given active ingredient combination obeys the so-called COLBY formula and can be calculated as follows (COLBY, S. R. "Calculating synergistic and antagonistic responses of herbicide combination". Weeds, Vol. 15, pages 20-22; 1967):

ppm=milligrams of active ingredient(=a.i.) per liter of spray mixture

X=% action by active ingredient A) using p ppm of active ingredient

Y=% action by active ingredient B) using q ppm of active ingredient.

According to COLBY, the expected (additive) action of active ingredients A)+B) using p+q ppm of active ingredient is $$E = X + Y - \frac{X \cdot Y}{100}$$

If the action actually observed (O) is greater than the expected action (E), then the action of the combination is super-additive, i.e. there is a synergistic effect. In mathematical terms the synergism factor SF corresponds to O/E. In the agricultural practice an SF of ≥1.2 indicates significant improvement over the purely complementary addition of activities (expected activity), while an SF of ≤0.9 in the practical application routine signals a loss of activity compared to the expected activity.

Example B-1: Activity Against *Ustilago nuda* on Barley a) Seed Application

After application of the formulated seed treatment onto *U. nuda*-infected seeds of winterbarley the seeds are sown in trays filled with field soil. The trays are transferred to a growth room and kept there for 2 days at 20° C. and then for 2 weeks at 2° C. After this period the trial is transferred to a greenhouse where a temperature of 15° C. and a 14 hr light period is provided until flowering. The following assessments are made: number of infected heads. The fungicide interactions in the combinations are calculated according to COLBY method.

b) Fungal Growth Assay

Conidia of the fungus from cryogenic storage were directly mixed into nutrient broth (PDB potato dextrose broth). After placing a (DMSO) solution of the test compounds into a microtiter plate (96-well format) the nutrient broth containing the fungal spores was added. The test plates were incubated at 24° C. and the inhibition of growth was determined photometrically after 48 hrs. The fungicide interactions in the combinations are calculated according to COLBY method.

| | Control of *Ustilago nuda* | | | | |
|---|---|---|---|---|---|
| | Dosage in mg active ingredient/ liter final medium ppm) | | | | Synergy |
| Cpd in ppm Fludioxonil | Racemic cpd Ia in ppm | Fludioxonil/Racemic cpd Ia in ppm/ppm | Expected control in % (% $C_{exp}$) | Observed control in % (% $C_{obs}$) | Factor SF = % $C_{obs}$/% $C_{exp}$ |
| 0.022 | — | — | — | 21 | — |
| 0.007 | — | — | — | 0 | — |
| 0.002 | — | — | — | 0 | — |
| — | 0.007 | — | — | 15 | — |
| — | 0.002 | — | — | 0 | — |
| — | 0.0001 | — | — | 5 | — |
| | | 0.022/0.007 | 33 | 43 | 1.3 |
| | | 0.022/0.002 | 21 | 25 | 1.2 |
| | | 0.007/0.007 | 15 | 30 | 2.0 |
| | | 0.002/0.0001 | 5 | 6 | 1.2 |

Control of *Ustilago nuda*

| Dosage in mg active ingredient/liter final medium ppm) | | | | | Synergy |
|---|---|---|---|---|---|
| Cpd in ppm Difenoconazole | Racemic cpd Ia in ppm | Difenoconazole/ Racemic cpd Ia in ppm/ppm | Expected control in % (% $C_{exp}$) | Observed control in % (% $C_{obs}$) | Factor SF = % $C_{obs}$/% $C_{exp}$ |
| 0.002 | — | — | — | 2 | — |
| — | 0.0003 | — | — | 0 | — |
| | | 0.002/0.0003 | 2 | 6 | 3.0 |

Example B-2: Activity Against *Microdochium nivale* on Wheat a) Seed Application After application of the formulated seed treatment onto *M. nivale*-infected seeds of winterwheat the seeds are sown in trays filled with planting soil. The trial is kept for 4 weeks in a growth room at 4° C. and darkness. Then the temperature is increased to 15° C. and a 12 hr light period is provided. After development of the primary leaf plants are kept at 10° C. and high humidity until the trial is finished. The following assessments are made: number of infected plants. The fungicide interactions in the combinations are calculated according to COLBY method.

b) Fungal Growth Assay

Conidia of the fungus from cryogenic storage were directly mixed into nutrient broth (PDB potato dextrose broth). After placing a (DMSO) solution of the test compounds into a microtiter plate (96-well format) the nutrient broth containing the fungal spores was added. The test plates were incubated at 24° C. and the inhibition of growth was measured photometrically after 72 hrs. The fungicide interactions in the combinations are calculated according to COLBY method.

Control of *Microdochium nivale*

| Dosage in mg active ingredient/liter final medium ppm) | | | | | Synergy |
|---|---|---|---|---|---|
| Cpd in ppm Fludioxonil | Racemic cpd Ia in ppm | Fludioxonil/Racemic cpd Ia in ppm/ppm | Expected control in % (% $C_{exp}$) | Observed control in % (% $C_{obs}$) | Factor SF = % $C_{obs}$/% $C_{exp}$ |
| 0.067 | — | — | — | 3 | — |
| 0.022 | — | — | — | 0 | — |
| 0.007 | — | — | — | 0 | — |
| 0.002 | — | — | — | 0 | — |
| — | 0.067 | — | — | 0 | — |
| — | 0.022 | — | — | 0 | — |
| — | 0.007 | — | — | 2 | — |
| — | 0.002 | — | — | 0 | — |
| — | 0.0008 | — | — | 0 | — |
| — | 0.0003 | — | — | 0 | — |
| | | 0.067/0.067 | 3 | 6 | 2.0 |
| | | 0.067/0.022 | 3 | 8 | 2.7 |
| | | 0.067/0.007 | 5 | 7 | 1.4 |
| | | 0.022/0.007 | 2 | 6 | 3.0 |
| | | 0.002/0.007 | 2 | 6 | 3.0 |

Control of *Microdochium nivale*

| Dosage in mg active ingredient/liter final medium ppm) | | | | | Synergy |
|---|---|---|---|---|---|
| Cpd in ppm Difenoconazole | Racemic cpd Ia in ppm | Difenoconazole/ Racemic cpd Ia in ppm/ppm | Expected control in % (% $C_{exp}$) | Observed control in % (% $C_{obs}$) | Factor SF = % $C_{obs}$/% $C_{exp}$ |
| 0.6 | — | — | — | 13 | — |
| 0.2 | — | — | — | 1 | — |
| 0.007 | — | — | — | 4 | — |
| — | 0.067 | — | — | 4 | — |
| — | 0.022 | — | — | 11 | — |
| — | 0.0025 | — | — | 1 | — |
| — | 0.0003 | — | — | 0 | — |
| | | 0.6/0.067 | 16 | 21 | 1.3 |
| | | 0.2/0.067 | 5 | 9 | 1.8 |
| | | 0.2/0.0003 | 1 | 2 | 2.0 |

Control of *Microdochium nivale*

| Cpd in ppm Difenoconazole | Racemic cpd Ia in ppm | Difenoconazole/ Racemic cpd Ia in ppm/ppm | Expected control in % (% $C_{exp}$) | Observed control in % (% $C_{obs}$) | Synergy Factor SF = % $C_{obs}$/% $C_{exp}$ |
|---|---|---|---|---|---|
| | | 0.007/0.0025 | 5 | 9 | 1.8 |
| | | 0.007/0.0003 | 4 | 5 | 1.3 |

Control of *Microdochium nivale*

| Cpd in ppm Cyproconazole | Racemic cpd Ia in ppm | Cyproconazole/ Racemic cpd Ia in ppm/ppm | Expected control in % (% $C_{exp}$) | Observed control in % (% $C_{obs}$) | Synergy Factor SF = % $C_{obs}$/% $C_{exp}$ |
|---|---|---|---|---|---|
| 1.8 | — | — | — | 9 | — |
| 0.6 | — | — | — | 0 | — |
| 0.2 | — | — | — | 0 | — |
| — | 0.067 | — | — | 2 | — |
| — | 0.022 | — | — | 0 | — |
| — | 0.0074 | — | — | 0 | — |
| — | 0.0025 | — | — | 0 | — |
| | | 1.8/0.067 | 11 | 18 | 1.7 |
| | | 1.8/0.022 | 9 | 13 | 1.5 |
| | | 1.8/0.0074 | 9 | 14 | 1.6 |
| | | 0.6/0.067 | 2 | 5 | 2.5 |
| | | 0.6/0.0074 | 0 | 6 | >100 |
| | | 0.2/0.022 | 0 | 7 | >100 |
| | | 0.2/0.0025 | 0 | 3 | >100 |

Example B-3: Activity Against *Pyrenophora graminea* on Barley a) Seed Application After application of the formulated seed treatment onto *P. graminea*-infected seeds of winterbarley the seeds are sown in trays filled with field soil. The trays are kept in a growth room for 3 weeks at 4° C. After this period the trial is transferred to a greenhouse where a temperature of 12° C. and a 14 hr light period is provided. The following assessments are made: number of infected plants. The fungicide interactions in the combinations are calculated according to COLBY method.

b) Fungal Growth Assay

Conidia of the fungus from cryogenic storage were directly mixed into nutrient broth (PDB potato dextrose broth). After placing a (DMSO) solution of the test compounds into a microtiter plate (96-well format) the nutrient broth containing the fungal spores was added. The test plates were incubated at 24° C. and the inhibition of growth was measured photometrically after 72 hrs. The fungicide interactions in the combinations are calculated according to COLBY method.

Control of *Pyrenophora graminea*

| Cpd in ppm Fludioxonil | Racemic cpd Ia in ppm | Fludioxonil/Racemic cpd Ia in ppm/ppm | Expected control in % (% $C_{exp}$) | Observed control in % (% $C_{obs}$) | Synergy Factor SF = % $C_{obs}$/% $C_{exp}$ |
|---|---|---|---|---|---|
| 0.002 | — | — | — | 7 | — |
| — | 1.8 | — | — | 11 | — |
| — | 0.2 | — | — | 1 | — |
| — | 0.002 | — | — | 0 | — |
| — | 0.0003 | — | — | 1 | — |
| | | 0.002/1.8 | 16 | 28 | 1.7 |
| | | 0.002/0.2 | 8 | 16 | 2.0 |
| | | 0.002/0.002 | 7 | 15 | 2.1 |
| | | 0.002/0.0003 | 7 | 13 | 1.8 |

| Control of *Pyrenophora graminea* | | | | | |
|---|---|---|---|---|---|
| Dosage in mg active ingredient/liter final medium ppm) | | | | | Synergy |
| Cpd in ppm Difenoconazole | Racemic cpd Ia in ppm | Difenoconazole/ Racemic cpd Ia in ppm/ppm | Expected control in % (% $C_{exp}$) | Observed control in % (% $C_{obs}$) | Factor SF = % $C_{obs}$/% $C_{exp}$ |
| 0.2 | — | — | — | 51 | — |
| 0.067 | — | — | — | 23 | — |
| 0.022 | — | — | — | 15 | — |
| 0.007 | — | — | — | 0 | — |
| — | 1.8 | — | — | 1 | — |
| — | 0.2 | — | — | 5 | — |
| — | 0.067 | — | — | 1 | — |
| — | 0.0074 | — | — | 4 | — |
| | | 0.2/1.8 | 52 | 64 | 1.2 |
| | | 0.067/1.8 | 24 | 38 | 1.6 |
| | | 0.022/1.8 | 16 | 26 | 1.6 |
| | | 0.007/1.8 | 2 | 24 | 12.0 |
| | | 0.007/0.2 | 5 | 16 | 3.2 |
| | | 0.007/0.067 | 1 | 11 | 11.0 |
| | | 0.007/0.0074 | 4 | 17 | 4.2 |

| Control of *Pyrenophora graminea* | | | | | |
|---|---|---|---|---|---|
| Dosage in mg active ingredient/liter final medium ppm) | | | | | Synergy |
| Cpd in ppm Cyproconazole | Racemic cpd Ia in ppm | Cyproconazole/ Racemic cpd Ia in ppm/ppm | Expected control in % (% $C_{exp}$) | Observed control in % (% $C_{obs}$) | Factor SF = % $C_{obs}$/% $C_{exp}$ |
| 0.6 | — | — | — | 28 | — |
| 0.2 | — | — | — | 19 | — |
| 0.022 | — | — | — | 4 | — |
| — | 1.8 | — | — | 6 | — |
| — | 0.022 | — | — | 0 | — |
| — | 0.0003 | — | — | 1 | — |
| | | 0.6/1.8 | 33 | 39 | 1.2 |
| | | 0.6/0.0003 | 29 | 36 | 1.2 |
| | | 0.2/0.0003 | 20 | 30 | 1.5 |
| | | 0.022/1.8 | 10 | 16 | 1.6 |
| | | 0.022/0.022 | 4 | 5 | 1.3 |

| Control of *Pyrenophora graminea* | | | | | |
|---|---|---|---|---|---|
| Dosage in mg active ingredient/liter final medium ppm) | | | | | Synergy |
| Cpd in ppm Thiabendazole | Racemic cpd Ia in ppm | Thiabendazole/ Racemic cpd Ia in ppm/ppm | Expected control in % (% $C_{exp}$) | Observed control in % (% $C_{obs}$) | Factor SF = % $C_{obs}$/% $C_{exp}$ |
| 0.0223 | — | — | — | 0 | — |
| 0.0025 | — | — | — | 0 | — |
| — | 0.2 | — | — | 48 | — |
| — | 0.0667 | — | — | 20 | — |
| — | 0.0008 | — | — | 6 | — |
| | | 0.0223/0.2 | 49 | 61 | 1.2 |
| | | 0.0025/0.2 | 48 | 63 | 1.3 |
| | | 0.0025/0.0667 | 20 | 27 | 1.4 |
| | | 0.0025/0.0008 | 6 | 8 | 1.3 |

Example B-4: Activity Against *Gäumannomyces graminis* on Wheat a) Seed Application After application of the formulated seed treatment onto seeds of winterwheat the seeds are sown in trays filled with field soil. The field soil has been inoculated artificially before sowing with *Gäumannomyces graminis* by thouroughly mixing mycelium and soil. The trial is kept in a growth room for 5 weeks at 17° C. and a 14 hr light period. The following assessments are made: disease severity on roots of infected plants. The fungicide interactions in the combinations are calculated according to COLBY method.

b) Fungal Growth Assay

Mycelial fragments of a newly grown culture of the fungus, were directly mixed into nutrient broth (PDB potato dextrose broth). After placing a (DMSO) solution of the test compounds into a microtiter plate (96-well format) the nutrient broth containing the fungal spores was added. The test plates were incubated at 24° C. and the inhibition of growth was measured photometrically after 72 hrs. The fungicide interactions in the combinations are calculated according to COLBY method.

| | Control of *Gaumannomyces graminis* | | | | |
|---|---|---|---|---|---|
| Dosage in mg active ingredient/liter final medium ppm) | | | | | Synergy |
| Cpd in ppm Azoxystrobin | Racemic cpd Ia in ppm | Azoxystrobin/ Racemic cpd Ia in ppm/ppm | Expected control in % (% $C_{exp}$) | Observed control in % (% $C_{obs}$) | Factor SF = % $C_{obs}$/% $C_{exp}$ |
| 0.002 | — | — | — | 11 | — |
| — | 0.2 | — | — | 0 | — |
| — | 0.007 | — | — | 0 | — |
| — | 0.002 | — | — | 2 | — |
| — | 0.0008 | — | — | 0 | — |
| — | 0.0003 | — | — | 0 | — |
| — | — | 0.002/0.2 | 11 | 21 | 1.9 |
| — | — | 0.002/0.007 | 11 | 19 | 1.7 |
| — | — | 0.002/0.002 | 13 | 18 | 1.4 |
| — | — | 0.002/0.0008 | 11 | 18 | 1.6 |
| — | — | 0.002/0.0003 | 11 | 15 | 1.3 |

Example B-5: Activity Against *Rhizoctonia solani* a) Seed Application

After application of the formulated seed treatment onto seeds of cotton the seeds are sown in trays filled with soil. The soil has been inoculated artificially before sowing with *Rhizoctonia solani* by thouroughly mixing mycelium and soil. The trial is kept in a growthroom for 2 weeks at 19° C. and then is transferred to a greenhouse at 23° C. A 14 hr light period is provided from the onset of germination. The following assessments are made: number of infected plants. The fungicide interactions in the combinations are calculated according to COLBY method.

b) Fungal Growth Assay

Mycelial fragments of the fungus from cryogenic storage were directly mixed into nutrient broth (PDB potato dextrose broth). After placing a (DMSO) solution of the test compounds into a microtiter plate (96-well format) the nutrient broth containing the fungal spores was added. The test plates were incubated at 24° C. and the inhibition of growth was determined photometrically after 48 hrs. The fungicide interactions in the combinations are calculated according to COLBY method.

| | Control of *Rhizoctonia solani* | | | | |
|---|---|---|---|---|---|
| Dosage in mg active ingredient/liter final medium ppm) | | | | | Synergy |
| Cpd in ppm Fludioxonil | Racemic cpd Ia in ppm | Fludioxonil/Racemic cpd Ia in ppm/ppm | Expected control in % (% $C_{exp}$) | Observed control in % (% $C_{obs}$) | Factor SF = % $C_{obs}$/% $C_{exp}$ |
| 0.067 | — | — | — | 0 | — |
| 0.022 | — | — | — | 0 | — |
| 0.007 | — | — | — | 6 | — |
| 0.002 | — | — | — | 0 | — |
| — | 0.007 | — | — | 4 | — |
| — | — | 0.067/0.007 | 4 | 21 | 5.2 |
| — | — | 0.022/0.007 | 4 | 47 | 11.8 |
| — | — | 0.007/0.007 | 10 | 37 | 3.7 |
| — | — | 0.002/0.007 | 4 | 36 | 9.0 |

| Control of *Rhizoctonia solani* | | | | | |
|---|---|---|---|---|---|
| Dosage in mg active ingredient/liter final medium ppm) | | | | | Synergy |
| Cpd in ppm Thiabendazole | Racemic cpd Ia in ppm | Thiabendazole/ Racemic cpd Ia in ppm/ppm | Expected control in % (% $C_{exp}$) | Observed control in % (% $C_{obs}$) | Factor SF = % $C_{obs}$/% $C_{exp}$ |
| 0.6 | — | — | — | 13 | — |
| 0.2 | — | — | — | 12 | — |
| 0.023 | — | — | — | 7 | — |
| 0.0074 | — | — | — | 0 | — |
| — | 0.0074 | — | — | 0 | — |
| — | 0.0025 | — | — | 4 | — |
| — | 0.0008 | — | — | 8 | — |
| — | 0.0001 | — | — | 3 | — |
| — | — | 0.6/0.0008 | 20 | 25 | 1.2 |
| — | — | 0.6/0.0001 | 15 | 24 | 1.6 |
| — | — | 0.2/0.0074 | 12 | 31 | 2.6 |
| — | — | 0.0223/0.0074 | 8 | 36 | 4.5 |
| — | — | 0.0223/0.0025 | 11 | 14 | 1.3 |
| — | — | 0.0223/0.0001 | 10 | 21 | 2.1 |
| — | — | 0.0074/0.0074 | 5 | 54 | 10.8 |
| — | — | 0.0074/0.0025 | 8 | 21 | 2.6 |
| — | — | 0.0074/0.0008 | 13 | 19 | 1.5 |
| — | — | 0.0074/0.0001 | 8 | 15 | 1.9 |

Example B-6: Activity Against *Septoria tritici*

Conidia of the fungus from cryogenic storage were directly mixed into nutrient broth (PDB potato dextrose broth). After placing a (DMSO) solution of the test compounds into a microtiter plate (96-well format) the nutrient broth containing the fungal spores was added. The test plates were incubated at 24° C. and the inhibition of growth was determined photometrically after 72 hrs. The fungicide interactions in the combinations are calculated according to COLBY method.

| Control of *Septoria tritici* | | | | | |
|---|---|---|---|---|---|
| Dosage in mg active ingredient/liter final medium ppm) | | | | | Synergy |
| Cpd in ppm Fludioxonil | Racemic cpd Ia in ppm | Fludioxonil/Racemic cpd Ia in ppm/ppm | Expected control in % (% $C_{exp}$) | Observed control in % (% $C_{obs}$) | Factor SF = % $C_{obs}$/% $C_{exp}$ |
| 0.067 | — | — | — | 9 | — |
| 0.002 | — | — | — | 0 | — |
| — | 0.067 | — | — | 4 | — |
| — | 0.022 | — | — | 0 | — |
| — | 0.007 | — | — | 0 | — |
| — | 0.0003 | — | — | 2 | — |
| — | — | 0.067/0.067 | 13 | 19 | 1.4 |
| — | — | 0.067/0.022 | 9 | 12 | 1.3 |
| — | — | 0.067/0.007 | 9 | 12 | 1.3 |
| — | — | 0.002/0.067 | 4 | 9 | 2.2 |
| — | — | 0.002/0.0003 | 2 | 8 | 4.0 |

| Control of *Septoria tritici* | | | | | |
|---|---|---|---|---|---|
| Dosage in mg active ingredient/liter final medium ppm) | | | | | Synergy |
| Cpd in ppm Thiabendazole | Racemic cpd Ia in ppm | Thiabendazole/ Racemic cpd Ia in ppm/ppm | Expected control in % (% $C_{exp}$) | Observed control in % (% $C_{obs}$) | Factor SF = % $C_{obs}$/% $C_{exp}$ |
| 1.8 | — | — | — | 1 | — |
| 0.6 | — | — | — | 3 | — |
| 0.067 | — | — | — | 0 | — |
| 0.0223 | — | — | — | 0 | — |
| — | 0.0074 | — | — | 0 | — |
| — | 0.0003 | — | — | 1 | — |
| — | 0.0001 | — | — | 0 | — |
| — | — | 1.8/0.0003 | 2 | 4 | 2.0 |

Control of *Septoria tritici*

| Dosage in mg active ingredient/liter final medium ppm) | | | | | Synergy |
|---|---|---|---|---|---|
| Cpd in ppm Thiabendazole | Racemic cpd Ia in ppm | Thiabendazole/ Racemic cpd Ia in ppm/ppm | Expected control in % (% $C_{exp}$) | Observed control in % (% $C_{obs}$) | Factor SF = % $C_{obs}$/% $C_{exp}$ |
| | | 1.8/0.0001 | 1 | 2 | 2.0 |
| | | 0.6/0.0074 | 3 | 7 | 2.3 |
| | | 0.6/0.0001 | 3 | 6 | 2.0 |
| | | 0.067/0.0003 | 1 | 5 | 5.0 |
| | | 0.0223/0.0003 | 1 | 3 | 3.0 |

Example B-7: Activity Against *Fusarium graminearum*

Conidia of the fungus from cryogenic storage were directly mixed into nutrient broth (PDB potato dextrose broth). After placing a (DMSO) solution of the test compounds into a microtiter plate (96-well format) the nutrient broth containing the fungal spores was added. The test plates were incubated at 24° C. and the inhibition of growth was determined photometrically after 48 hrs. The fungicide interactions in the combinations are calculated according to COLBY method.

Control of *Fusarium graminearum*

| Dosage in mg active ingredient/liter final medium ppm) | | | | | Synergy |
|---|---|---|---|---|---|
| Cpd in ppm Fludioxonil | Racemic cpd Ia in ppm | Fludioxonil/Racemic cpd Ia in ppm/ppm | Expected control in % (% $C_{exp}$) | Observed control in % (% $C_{obs}$) | Factor SF = % $C_{obs}$/% $C_{exp}$ |
| 0.067 | — | — | — | 39 | — |
| 0.022 | — | — | — | 6 | — |
| 0.007 | — | — | — | 1 | — |
| — | 0.6 | — | — | 12 | — |
| — | 0.2 | — | — | 7 | — |
| — | 0.067 | — | — | 4 | — |
| — | 0.007 | — | — | 0 | — |
| — | 0.0008 | — | — | 0 | — |
| | | 0.067/0.6 | 46 | 58 | 1.2 |
| | | 0.067/0.2 | 43 | 56 | 1.3 |
| | | 0.067/0.067 | 41 | 54 | 1.3 |
| | | 0.022/0.6 | 17 | 21 | 1.2 |
| | | 0.022/0.067 | 9 | 19 | 2.1 |
| | | 0.007/0.007 | 1 | 2 | 2.0 |
| | | 0.007/0.0008 | 1 | 5 | 5.0 |

Control of *Fusarium graminearum*

| Dosage in mg active ingredient/liter final medium ppm) | | | | | Synergy |
|---|---|---|---|---|---|
| Cpd in ppm Cyproconazole | Racemic cpd Ia in ppm | Cyproconazole/ Racemic cpd Ia in ppm/ppm | Expected control in % (% $C_{exp}$) | Observed control in % (% $C_{obs}$) | Factor SF = % $C_{obs}$/% $C_{exp}$ |
| 0.2 | — | — | — | 0 | — |
| 0.022 | — | — | — | 1 | — |
| 0.002 | — | — | — | 5 | — |
| — | 0.067 | — | — | 10 | — |
| — | 0.022 | — | — | 0 | — |
| — | 0.0074 | — | — | 0 | — |
| — | 0.0001 | — | — | 0 | — |
| | | 0.2/0.022 | 0 | 3 | >100 |
| | | 0.2/0.0074 | 0 | 2 | >100 |
| | | 0.2/0.0001 | 0 | 2 | >100 |
| | | 0.022/0.22 | 1 | 2 | 2.0 |
| | | 0.002/0.0001 | 5 | 7 | 1.4 |

Control of *Fusarium graminearum*

| Cpd in ppm Thiabendazole | Racemic cpd Ia in ppm | Thiabendazole/ Racemic cpd Ia in ppm/ppm | Expected control in % (% $C_{exp}$) | Observed control in % (% $C_{obs}$) | Synergy Factor SF = % $C_{obs}$/% $C_{exp}$ |
|---|---|---|---|---|---|
| 0.0223 | — | — | — | 0 | — |
| 0.0025 | — | — | — | 1 | — |
| — | 1.8 | — | — | 18 | — |
| — | 0.0667 | — | — | 7 | — |
| — | 0.0074 | — | — | 0 | — |
| | | 0.0223/1.8 | 18 | 22 | 1.2 |
| | | 0.0223/0.0667 | 7 | 9 | 1.2 |
| | | 0.0025/1.8 | 19 | 27 | 1.4 |
| | | 0.0025/0.0074 | 1 | 3 | 3.0 |

The combinations according to the invention exhibit good activity in all of the above examples, where no individually specified data are reported.

What is claimed is:

1. A method of controlling phytopathogenic diseases on useful plants or on propagation material thereof, which comprises applying to the useful plants, the locus thereof or propagation material thereof a combination of components A) and B) in a synergistically effective amount, wherein component A) is a compound of formula I

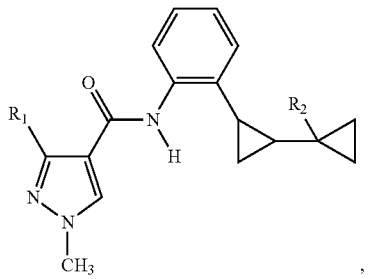

wherein
$R_1$ is difluoromethyl and
$R_2$ is hydrogen; or a tautomer of such a compound; and component B) is thiabendazole; and wherein the weight ratio of A) to B) is between 720:1 and 0.00006:1.

2. The method according to claim 1, wherein component A) includes a mixture of compounds of formula $I_I$ and formula $I_{II}$

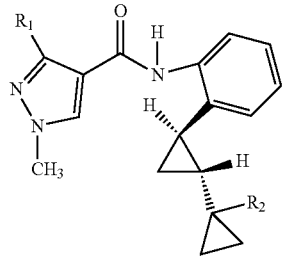

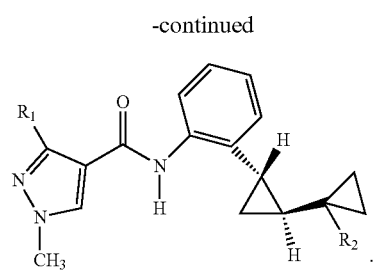

3. The method according to claim 2, wherein the mixture of compounds of formula $I_I$ and formula $I_{II}$ is from 65 to 99% by weight of component A).

4. A fungicidal composition comprising a combination of components A) and B) in a synergistically effective amount together with an agriculturally acceptable carrier, and optionally a surfactant, wherein
component A) is a compound of formula I

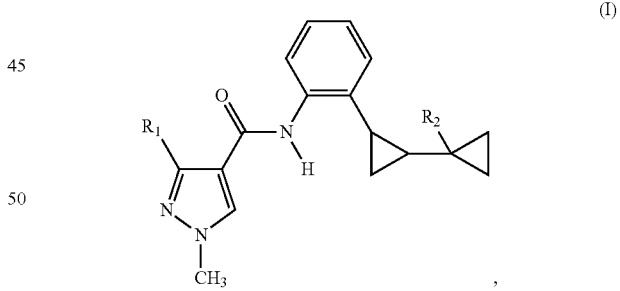

wherein
$R_1$ is difluoromethyl and
$R_2$ is hydrogen; or a tautomer of such a compound; and component B) is thiabendazole; and wherein the weight ratio of A) to B) is between 720:1 and 0.00006:1.

* * * * *